(12) United States Patent
Carlsen et al.

(10) Patent No.: US 7,549,419 B2
(45) Date of Patent: *Jun. 23, 2009

(54) HEAT AND MOISTURE EXCHANGER ADAPTOR FOR CLOSED SUCTION CATHETER ASSEMBLY AND SYSTEM CONTAINING THE SAME

(75) Inventors: Wayne D. Carlsen, Riverton, UT (US); Chet M. Crump, Draper, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 915 days.

This patent is subject to a terminal disclaimer.

(21) Appl. No.: 10/874,466

(22) Filed: Jun. 23, 2004

(65) Prior Publication Data

US 2004/0255952 A1    Dec. 23, 2004

Related U.S. Application Data

(63) Continuation-in-part of application No. 09/702,376, filed on Oct. 31, 2000, now Pat. No. 6,769,430.

(51) Int. Cl.
*A62B 18/08* (2006.01)
(52) U.S. Cl. ............................ 128/201.13; 128/203.16; 128/203.26; 128/204.17; 128/207.14
(58) Field of Classification Search ............ 128/201.13, 128/205.27, 202.27, 912, 207.14, 203.26, 128/204.17, 203.16; 604/523, 533, 534, 604/535, 537, 538, 905, 284, 19, 508
See application file for complete search history.

(56) References Cited

U.S. PATENT DOCUMENTS

| | | | |
|---|---|---|---|
| 3,556,097 A | 1/1971 | Wallace | |
| 3,782,083 A | 1/1974 | Rosenberg | |
| 3,815,754 A | 6/1974 | Rosenberg | |
| 3,825,001 A | 7/1974 | Bennet et al. | |
| 3,831,629 A | 8/1974 | Mackal et al. | |
| 3,834,388 A | 9/1974 | Sauer | |
| 3,881,482 A | 5/1975 | Lindholm | |
| 3,902,500 A | 9/1975 | Dryden | |
| 3,932,153 A | 1/1976 | Byrns | |
| 3,937,220 A | 2/1976 | Coyne | |
| 3,991,762 A | 11/1976 | Radford | |
| 4,009,720 A | 3/1977 | Crandall | |
| 4,015,336 A | 4/1977 | Johnson | |
| 4,036,616 A | 7/1977 | Byrns | |

(Continued)

FOREIGN PATENT DOCUMENTS

EP            0265163         4/1988

(Continued)

*Primary Examiner*—Steven O Douglas
(74) *Attorney, Agent, or Firm*—James B. Robinson; William W. Letson

(57) ABSTRACT

A heat and moisture exchanger (HME) adaptor for a closed suction catheter assembly having one end in communication with a closed suction catheter assembly and another end configured to rotationally engage and releasably hold the HME is disclosed herein. The adaptor may include a retainer having an aperture that engages projections on the HME to releasably secure the adaptor to the HME. The adaptor may include a retaining ring that may be deformed or rotated to engage or disengage projections on the HME. The adaptor may be used with extended use closed suction catheter assemblies.

27 Claims, 13 Drawing Sheets

U.S. PATENT DOCUMENTS

| | | | |
|---|---|---|---|
| 4,047,527 A | 9/1977 | Kelsen | |
| 4,062,363 A | 12/1977 | Bonner, Jr. | |
| 4,090,513 A | 5/1978 | Togawa | |
| 4,159,954 A | 7/1979 | Gangemi | |
| 4,193,406 A | 3/1980 | Jinotti | |
| 4,291,691 A | 9/1981 | Cabal et al. | |
| 4,315,505 A | 2/1982 | Crandall et al. | |
| 4,327,723 A | 5/1982 | Frankhouser | |
| 4,351,328 A | 9/1982 | Bodai | |
| 4,405,163 A | 9/1983 | Voges et al. | |
| 4,468,224 A | 8/1984 | Enzmann et al. | |
| 4,508,533 A | 4/1985 | Abramson | |
| 4,516,573 A | 5/1985 | Gedeon | |
| 4,569,344 A | 2/1986 | Palmer | |
| 4,573,965 A | 3/1986 | Russo | |
| 4,573,979 A | 3/1986 | Blake | |
| 4,574,173 A | 3/1986 | Bennett | |
| 4,595,005 A | 6/1986 | Jinotti | |
| 4,638,539 A | 1/1987 | Palmer | |
| 4,646,733 A | 3/1987 | Stroh et al. | |
| 4,649,913 A | 3/1987 | Watson | |
| 4,657,008 A | 4/1987 | Broddner et al. | |
| 4,669,463 A | 6/1987 | McConnell | |
| 4,696,296 A | 9/1987 | Palmer | |
| 4,696,305 A | 9/1987 | Von Berg | |
| 4,705,073 A | 11/1987 | Beck | |
| 4,798,676 A | 1/1989 | Matkovich | |
| 4,805,611 A | 2/1989 | Hodgkins | |
| 4,825,859 A | 5/1989 | Lambert | |
| 4,834,726 A | 5/1989 | Lambert | |
| 4,836,199 A | 6/1989 | Palmer | |
| 4,850,350 A | 7/1989 | Jackson | |
| 4,852,563 A | 8/1989 | Gross | |
| 4,872,579 A | 10/1989 | Palmer | |
| 4,909,248 A | 3/1990 | McLennan Anderson | |
| 4,929,426 A | 5/1990 | Bodai et al. | |
| 4,938,741 A | 7/1990 | Lambert | |
| 4,946,445 A | 8/1990 | Lynn | |
| 4,967,743 A | 11/1990 | Lambert | |
| 4,969,878 A | 11/1990 | Schmidt et al. | |
| D312,880 S | 12/1990 | Bodai et al. | |
| 5,029,580 A | 7/1991 | Radford et al. | |
| 5,042,468 A | 8/1991 | Lambert | |
| D321,252 S | 10/1991 | Jepson et al. | |
| 5,060,646 A | 10/1991 | Page | |
| 5,067,496 A | 11/1991 | Eisele | |
| 5,073,164 A | 12/1991 | Hollister et al. | |
| 5,083,561 A | 1/1992 | Russo | |
| 5,088,486 A | 2/1992 | Jinotti | |
| 5,101,817 A | 4/1992 | Etter | |
| 5,104,389 A | 4/1992 | Deem et al. | |
| 5,107,829 A | 4/1992 | Lambert | |
| 5,109,471 A | 4/1992 | Lang | |
| 5,125,893 A | 6/1992 | Dryden | |
| 5,134,996 A | 8/1992 | Bell | |
| 5,139,018 A | 8/1992 | Brodsky et al. | |
| 5,140,983 A | 8/1992 | Jinotti | |
| 5,158,569 A | 10/1992 | Strickland et al. | |
| 5,184,611 A | 2/1993 | Turnbull | |
| 5,191,881 A | 3/1993 | Beck | |
| 5,195,527 A | 3/1993 | Hicks | |
| 5,201,309 A | 4/1993 | Friberg et al. | |
| 5,201,717 A | 4/1993 | Wyatt et al. | |
| 5,213,096 A | 5/1993 | Kihlberg et al. | |
| 5,215,522 A | 6/1993 | Page et al. | |
| 5,220,916 A | 6/1993 | Russo | |
| 5,230,332 A | 7/1993 | Strickland | |
| 5,242,084 A | 9/1993 | Jinotti | |
| 5,254,098 A | 10/1993 | Ulrich et al. | |
| 5,255,676 A | 10/1993 | Russo | |
| 5,277,177 A | 1/1994 | Page et al. | |
| 5,300,043 A | 4/1994 | Devlin et al. | |
| 5,309,902 A | 5/1994 | Kee et al. | |
| 5,309,904 A | 5/1994 | Beck | |
| 5,325,850 A | 7/1994 | Ulrich et al. | |
| 5,325,851 A | 7/1994 | Reynolds et al. | |
| 5,333,606 A | 8/1994 | Schneider et al. | |
| 5,333,607 A | 8/1994 | Kee et al. | |
| 5,337,780 A | 8/1994 | Kee | |
| 5,343,857 A | 9/1994 | Schneider et al. | |
| 5,346,478 A | 9/1994 | Jinotti | |
| 5,349,950 A | 9/1994 | Ulrich et al. | |
| 5,354,267 A | 10/1994 | Niermann et al. | |
| 5,355,876 A | 10/1994 | Brodsky et al. | |
| 5,357,946 A | 10/1994 | Kee et al. | |
| 5,368,017 A | 11/1994 | Sorenson et al. | |
| 5,370,610 A | 12/1994 | Reynolds | |
| 5,383,447 A | 1/1995 | Lang | |
| 5,390,668 A | 2/1995 | Lehman | |
| 5,390,669 A | 2/1995 | Stuart et al. | |
| 5,435,298 A | 7/1995 | Anthony | |
| 5,445,141 A | 8/1995 | Kee et al. | |
| 5,449,348 A | 9/1995 | Dryden | |
| 5,460,172 A | 10/1995 | Eckerbom et al. | |
| 5,460,176 A | 10/1995 | Frigger | |
| 5,460,613 A | 10/1995 | Ulrich et al. | |
| 5,487,381 A | 1/1996 | Jinotti | |
| 5,490,503 A | 2/1996 | Hollister | |
| 5,496,287 A | 3/1996 | Jinotti | |
| 5,513,627 A | 5/1996 | Flam | |
| 5,513,628 A | 5/1996 | Coles et al. | |
| D373,637 S | 9/1996 | Spearman | |
| 5,578,006 A | 11/1996 | Schön | |
| 5,582,161 A | 12/1996 | Kee | |
| 5,582,165 A | 12/1996 | Bryan et al. | |
| 5,590,644 A | 1/1997 | Rosenkoetter | |
| 5,598,840 A | 2/1997 | Iund et al. | |
| 5,605,149 A | 2/1997 | Warters | |
| 5,628,306 A | 5/1997 | Kee | |
| 5,642,726 A | 7/1997 | Owens et al. | |
| 5,664,564 A | 9/1997 | Palmer | |
| 5,664,594 A | 9/1997 | Kee | |
| 5,676,136 A | 10/1997 | Russo | |
| 5,687,714 A | 11/1997 | Kolobow et al. | |
| 5,701,891 A | 12/1997 | Groenke | |
| 5,715,815 A | 2/1998 | Lorenzen et al. | |
| D393,722 S | 4/1998 | Fangrow, Jr. et al. | |
| 5,735,271 A | 4/1998 | Lorenzen et al. | |
| 5,769,702 A | 6/1998 | Hanson | |
| 5,775,325 A | 7/1998 | Russo | |
| 5,813,402 A | 9/1998 | Jinotti | |
| 5,855,562 A | 1/1999 | Moore et al. | |
| 5,882,348 A | 3/1999 | Winterton et al. | |
| 5,906,201 A | 5/1999 | Nilson | |
| 5,919,174 A | 7/1999 | Hanson | |
| 5,992,413 A | 11/1999 | Martin, Jr. et al. | |
| 6,033,455 A | 3/2000 | Kurashima | |
| 6,095,135 A | 8/2000 | Clawson et al. | |
| 6,105,576 A | 8/2000 | Clawson et al. | |
| 6,131,573 A | 10/2000 | Brown | |
| 6,165,168 A | 12/2000 | Russo | |
| 6,227,200 B1 | 5/2001 | Crump et al. | |
| 6,248,099 B1 | 6/2001 | Bell | |
| 6,363,930 B1 | 4/2002 | Clawson et al. | |
| 6,422,235 B1 | 7/2002 | Persson | |
| 6,543,451 B1 | 4/2003 | Crump et al. | |
| 6,588,427 B1 | 7/2003 | Carlsen et al. | |
| 6,602,219 B2 | 8/2003 | Madsen et al. | |
| 6,609,520 B1 | 8/2003 | Carlsen et al. | |
| 6,769,430 B1 | 8/2004 | Carlsen et al. | |

FOREIGN PATENT DOCUMENTS

EP 0730878 9/1996

| WO | WO 97/21386 | 6/1997 | WO | WO 00/02610 | 1/2000 |
| WO | WO 99/03525 | 1/1999 | WO | WO 01/72365 | 10/2001 |

HEAT AND MOISTURE EXCHANGER ADAPTOR FOR CLOSED SUCTION CATHETER ASSEMBLY AND SYSTEM CONTAINING THE SAME

This application is a continuation-in-part of application Ser. No. 09/702,376 entitled Heat and Moisture Exchanger Adaptor for Closed Suction Catheter Assembly and System Containing the Same filed in the U.S. Patent and Trademark Office on Oct. 31, 2000 now U.S. Pat. No. 6,769,430. The entirety of application Ser. No. 09/702,376 is hereby incorporated by reference.

BACKGROUND OF THE INVENTION

There are a number of different circumstances in which it is necessary for a person to have an artificial airway, such as a tracheostomy tube, placed in his or her respiratory tract. As used herein, the phrase "artificial airway" includes devices such as tracheostomy tubes, endotracheal tubes and the like. Artificial airways keep the patient's natural airway open so that adequate lung ventilation can be maintained. In particular situations, the artificial airway must be left in the patient for a prolonged period of time. For example, many persons suffering severe neck or head trauma receive a tracheostomy tube in conjunction with mechanical ventilation during extended recovery and rehabilitation periods.

When an artificial airway is used, it is critical that respiratory secretions be periodically removed. This is typically accomplished by the use of a respiratory suction catheter that is advanced into and through the tracheostomy tube. As the suction catheter is withdrawn, a negative pressure (or vacuum) is applied to draw mucus and other secretions from the patient's airways and the interior of the artificial airway. While a substantial amount of mucus and other secretions will be withdrawn through the lumen of the suction catheter, a portion of the mucus and other secretions will remain as a film on the outside of the catheter.

In a closed suction catheter assembly (for example as set forth in U.S. Pat. Nos. 3,991,762 and 4,569,344), the catheter may be enveloped by a protective sleeve and include a valve mechanism disposed near the vacuum source. These features reduce the risk of contamination to both the patient and the care-giver.

In normal breathing, the structures of the nose and sinus passages serve to heat and moisturize inhaled air. In situations where a patient requires mechanical ventilation on a periodic basis, it is common to place a heat and moisture exchanger (HME) on the proximal end of the artificial airway after removal of the mechanical ventilator. This type of placement is commonly done with patients who are able to breathe on their own for an extended period of time. In such systems and as used herein, "proximal" refers to the direction toward the clinician and "distal" refers to the direction toward the patient.

The HME is intended to replicate these functions, of heating and moisturizing air, in patients having artificial airways. The HME is adapted to reduce heat and moisture loss from the respiratory system of the patient as the patient breathes. This is done by retaining within the HME heat and moisture from air which is exhaled through the HME, and by warming and moisturizing air that is inhaled through the HME. The HME typically includes a material, such as porous foam, that is enclosed within a housing or other structure.

To date, most HMEs have not been used in conjunction with a closed suction catheter assembly. Thus, prior to suctioning respiratory secretions from a patient, it may be necessary to remove the HME from the proximal end of the artificial airway so that a suctioning catheter may be advanced to the patient's natural airways. Removal and attachment of the HME often causes discomfort to the patient and, during the period in which the HME has been removed, the patient is deprived of heat and moisture exchange and may be deprived of supplemental oxygen, if used.

Thus, there is a need for an inexpensive adaptor that enables a closed suction catheter to be easily and quickly attached to and removed from an HME that is mounted to an artificial airway while minimizing patient discomfort.

SUMMARY OF THE INVENTION

In response to the difficulties and problems discussed above, an adaptor which is adapted to connect a closed suction catheter to a HME has been developed.

The present invention is generally directed to an adaptor for connecting a closed suction catheter assembly to an HME mounted on an artificial airway, such as a tracheostomy tube. In addition, the present invention is directed to a closed suction catheter system containing the adaptor and a closed suction catheter assembly. The adaptor of the present invention does not interfere with patient breathing.

The adaptor has a first end that is adapted to be in communication with the closed suction catheter assembly. The adaptor may be removably or non-removably engaged with the catheter assembly. The adaptor also has a second end which is adapted to rotationally engage the heat and moisture exchanger. Further, there is a channel formed through the adaptor. This channel allows an aspirating catheter of the closed suction catheter assembly to be moved through the adaptor. The aspirating catheter can then also be moved through an aperture formed through the heat and moisture exchanger.

An adaptor cover may also be provided for use with the closed suction catheter system. The cover is configured to selectively isolate the closed suction catheter assembly from the environment, and to facilitate cleaning of the catheter after suctioning.

The present invention may also provide an alternative aspect of an adaptor for connecting a closed suction catheter assembly to an HME. The adaptor includes a first end configured for attachment to a closed suction catheter assembly, and a second end including a retainer capable of rotationally engaging the HME. The adaptor is configured for advancement of a catheter therethrough. The retainer may include a ring, for example a circular ring member, having a wall configured to encircle and releasably engage the HME.

Furthermore, if a ring retainer is included in the adaptor, the ring may include a pair of oppositely disposed apertures located on first and second portions of the ring. The apertures are configured to engage the HME. Moreover, the retaining ring may also include deflectable or deformable third and fourth portions oppositely disposed from each other on the ring disposed between the first and second portions on the ring. These deflectable or deformable portions may be such that application of pressure thereto allows the first and second sections to be able to outwardly bow from protrusions which may be present on the sides of an HME, thereby facilitating engagement and/or disengagement of apertures or the like with those protrusions.

The retainer of the adaptor may be formed such that the first portion and the second portion are defined by apertures for receiving external projections of the HME. Alternatively, the retainer may include at least one L-shaped channel configured for receiving external projections of the HME. In one aspect, the adaptor may also include an annular projection configured for engaging a valve in the top of the HME.

The present invention may also form an adaptor assembly for connecting a closed suction catheter assembly to an HME. The adaptor assembly includes an adaptor having a first end configured for attachment to a closed suction catheter assembly and a second end including a retainer configured for rotationally engaging the HME and positioning the closed suction catheter assembly with respect to the HME. The adaptor is configured for advancement of a catheter therethrough. The adaptor assembly may also contain an annular projection defining a channel through which a catheter of the closed suction catheter assembly may be advanced. The adaptor assembly may also include an adaptor cover configured for attachment to the annular projection.

The present invention is also directed to a closed suction catheter system. This system includes a closed suction catheter assembly having a catheter and a protective sleeve enveloping the catheter. The closed suction catheter assembly includes a distal end and an adaptor connected to this distal end capable of rotationally engaging a proximal end of an HME.

The invention will be more fully understood and further features and advantages will become apparent when reference is made to the following detailed description of exemplary aspects of the invention and the accompanying drawings.

BRIEF DESCRIPTION OF THE DRAWINGS

The purpose and advantages of the present invention will be apparent to those skilled in the art from the following detailed description in conjunction with the appended drawings in which.

DETAILED DESCRIPTION OF THE PRESENT INVENTION

Figure 1:
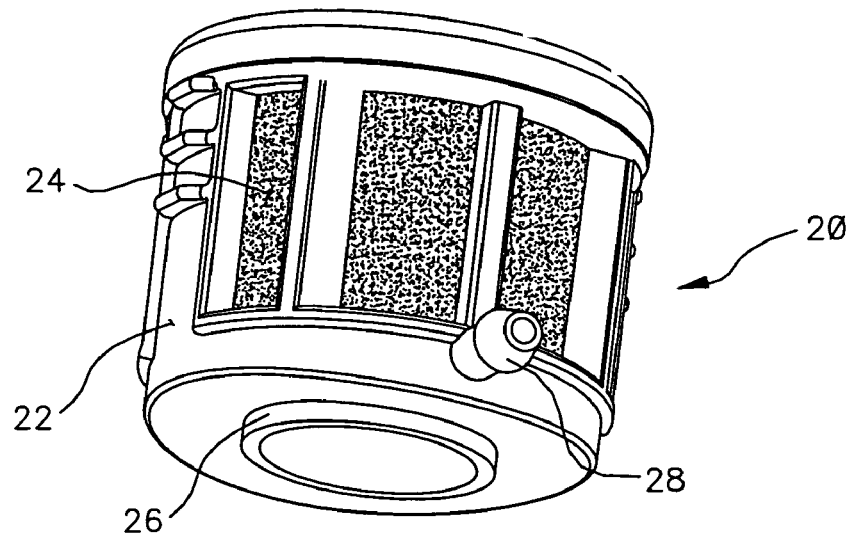
FIG. 1 is a perspective view of a heat and moisture exchanger (HME) in accordance with the teachings of the prior art.

The following detailed description will be made in the context of an adaptor which is adapted for medical use. It is readily apparent, however, that the adaptor would also be suitable for use with other types of systems, circuits or conduits and the like and is not intended to be limited to medical devices or use in a medical field. In addition, the invention will be described in the context of its various configurations. It should be appreciated that alternative arrangements of the invention can comprise any combination of such configurations. As such, the use of a desired aspect for ease in understanding and describing the invention shall not, in any manner, limit the scope of the invention.

Reference will now be made in detail to aspects of the invention, one or more examples of which are shown in the drawings. Various elements of the present invention will be given numeral designations and the invention will be discussed so as to enable one skilled in the art to make and use the invention. It should be appreciated that each example is provided by way of explaining the invention, and not as a limitation of the invention. For example, features illustrated or described with respect to one aspect may be used with another aspect to yield still a further aspect. These and other modifications and variations are within the scope and spirit of the invention.

The invention relates to a closed suction catheter assembly. At its distal end, which is the end nearest the patient once a closed suction catheter is attached, the closed suction catheter assembly may be attached to an artificial airway via one of a variety of connectors, including, for example, a multi-legged tracheostomy connector. One of the legs of the tracheostomy connector may be connected to a tracheostomy tube. With the use of the closed suction catheter assembly and a single catheter may be used for an extended period, typically a 24-hour to 72-hour period depending on the type of catheter selected. The patient may need to have the air drawn in through the artificial airway heated and moistened since the air is no longer traveling through the nose, sinuses, or throat where the temperature and moisture of air about to enter a person's lungs is generally adjusted. To accomplish this task, it is commonly the case that a heat and moisture exchanger be placed in the respiratory system.

A representative heat and moisture exchanger (HME) is shown in FIG. 1 at 20. As illustrated therein, the HME includes a housing 22 with a porous material 24 disposed within the housing. The porous material 24 is designed to reduce heat and moisture loss as the patient breathes. Heat and moisture within exhaled air is retained within the porous material 24. The inhaled air is warmed and humidified as the inhaled air passes through the porous material 24. The porous material 24 is typically a foam material that has sufficient porosity to reduce the loss of heat and moisture from the patient. The material is sometimes treated with a hygroscopic salt to enhance performance. Exemplary porous materials include corrugated paper, cellulose media, and polypropylene foam. The housing 22 includes a bottom port 26 for receiving an exposed end of a tracheostomy tube or other artificial airway.

The HME 20 may also include a side port 28 that may connect to an oxygen supply line to administer oxygen to the patient. Oxygen may be required by those, for instance, with emphysema and other diseases that cause damage to the lung tissue.

Figure 2:
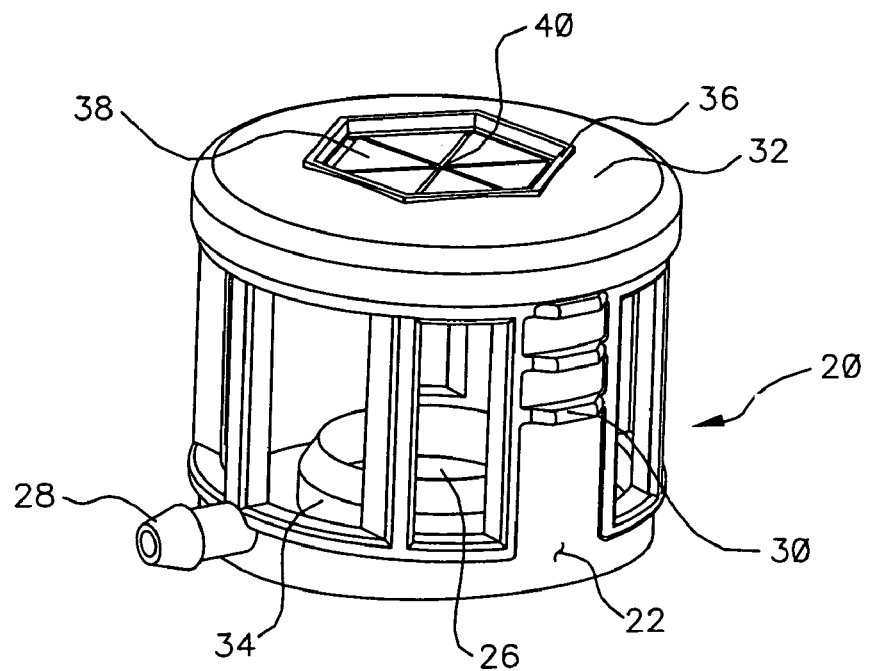
FIG. 2 is a perspective view of another HME in accordance with the teachings of the prior art.

FIG. 2 shows an additional conventional heat and moisture exchanger that is available from Datex-Ohmeda of Helsinki, Finland. The HME, generally indicated again at 20, includes a housing 22 having ridges 30, and a top surface 32 that forms the upper portion of the housing 22. In some aspects, the top surface 32 is configured as a removable cover that engages the housing 22. The ridges 30 enable a clinician to securely hold the housing while the housing 22 is being attached to or removed from a tracheostomy tube or other artificial airway. The housing 22 also includes an enclosure 34 into which material, such as the material 24, may be placed. The housing 22 further includes a bottom port 26, which is used to connect the HME 20 to a tracheostomy tube or other artificial airway. Further, the HME 20 in FIG. 2 illustrates optional side port 28.

While the HME 20 shown in FIG. 2 has ridges 30 of a certain size and shape, it will be appreciated, as discussed throughout the disclosure hereof, that the ridges shown are but just one of the suitable protrusions, recesses, and/or like which may be included on an HME with which rotational engagement of a catheter assembly or the like is desired. Exemplary protrusions, recesses, and the like which may be included on such an HME are described throughout this specification.

Disposed in alignment with the bottom port 26 is a top port 36 that is positioned in the center of the top surface 32. The bottom port 26 and the top port 36 are ends of a control aperture. The top port 36 is covered by a plurality of triangular-shaped projections 38 which are pivotably attached to the top surface 32 to enclose the top port 36 and form a valve 40. During attachment of the HME to an adaptor 42 (described in greater detail below), an annular projection of the adaptor 44 (see FIGS. 3, 5, and 9) contacts the triangular-shaped projections 38 causing the projections 38 to be deflected away from the annular projection 44 and open the valve 40. Thus, in practice, a clinician can suction a patient using the HME 20 by advancing a catheter (not shown) through the top port 36 and into the tracheostomy tube or artificial airway (not shown). It is appreciated that HMEs with other types of valves 40 exist. It is contemplated that all valve types on such an HME with which the adaptor will work are contemplated to be within the scope of the present invention. It is also contemplated that alternate projections 38 or projections having alternate orientations may be used. Suitable alternate shaped or configured projections 44 which extend from the adaptor 42 are also contemplated. Designing or constructing such alternate projections 44 to be compatible with different projections 38 of valve 40 would be within the capabilities of one having ordinary skill in the art after considering the teachings herein.

Figure 3:
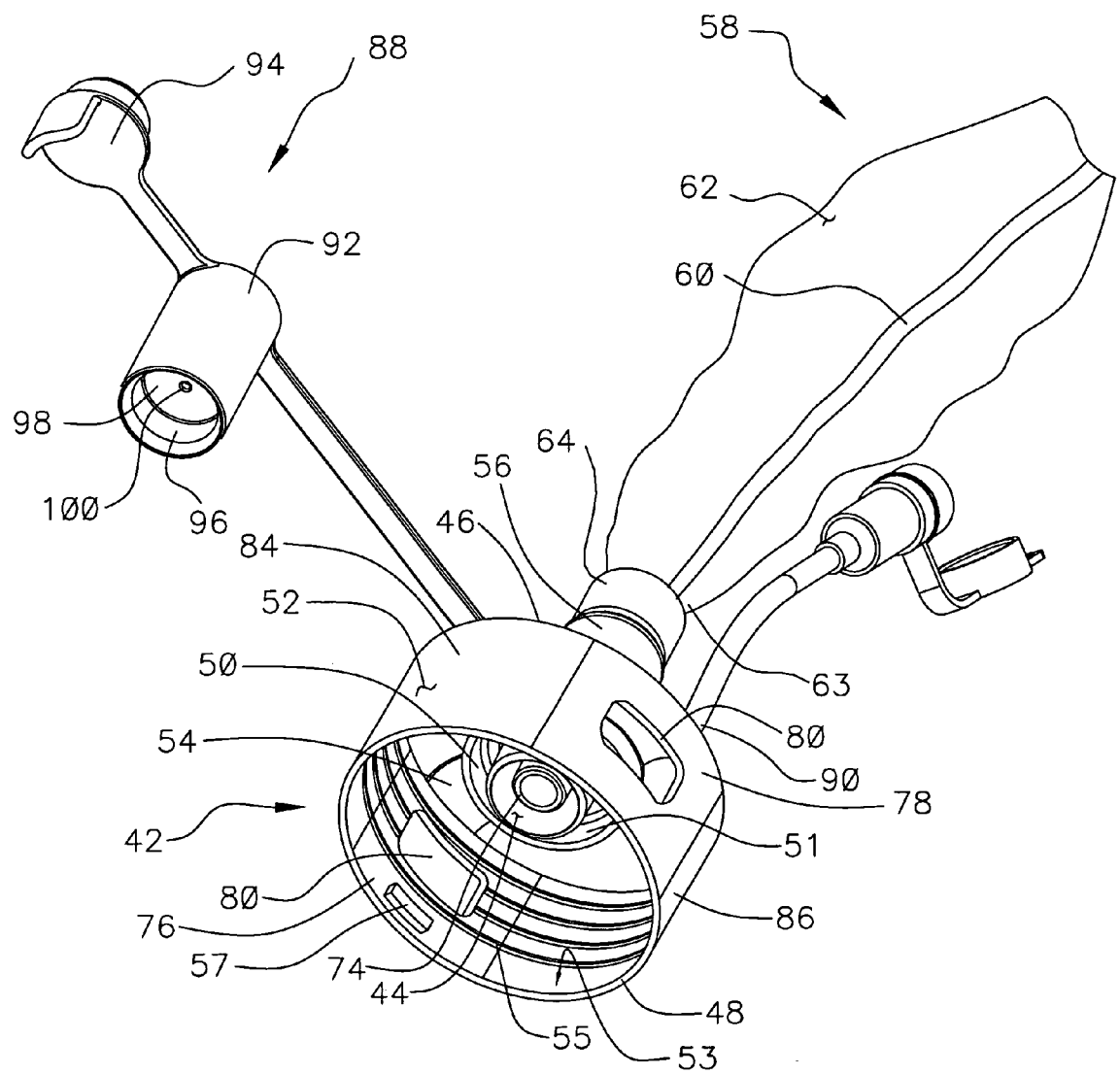
FIG. 3 is a perspective view of an adaptor of the present invention.

FIG. 3 shows a perspective view of an adaptor, generally indicated at 42, made in accordance with the principles of the present invention. The adaptor 42 has a proximal side 46 that is the side of the adaptor 42 that is attached to a closed suction catheter assembly 58. The adaptor 42 may be an integral or non-removable component of the catheter assembly 58 or can be configured to be releasably engaged to the closed suction catheter assembly 58 by any suitable manner. The adaptor 42 also has a distal side 48 that is configured for attachment to an HME (not shown).

The adaptor 42 includes a base 50 and a retaining structure configured with the base. In this aspect, the retaining structure is a retainer 52 attached to the base 50 by at least two arms 54.

Figure 11:
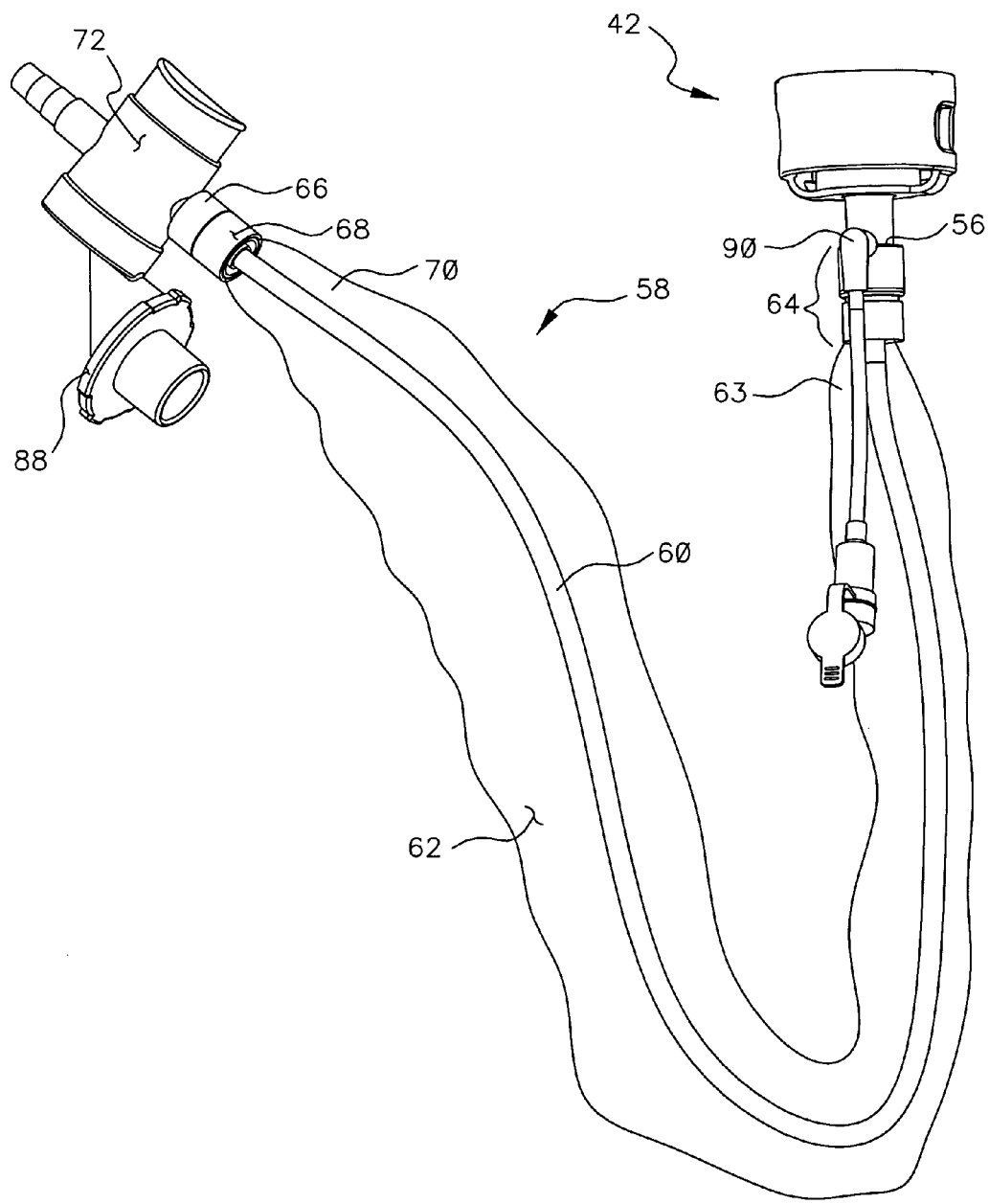
FIG. 11 is a side view of a closed suction catheter system with an adaptor and an adaptor cover.

As shown in FIG. 3, the retainer 52 takes the form of a retaining ring. The base 50, in turn, is connected to the distal end 56 of the closed suction catheter assembly 58. The closed suction catheter assembly 58 is shown fully in FIG. 11 and is partially shown in FIG. 3. The assembly includes an elongated aspirating catheter 60, an elongated protective sleeve 62 surrounding the catheter 60, and a coupling 64 which receives catheter 60 and secures the distal end 63 of the protective sleeve 62, thereby sealing the protective sleeve 62 about the catheter 60. The catheter 60 can be advanced through the coupling 64 and into an artificial airway such as a tracheostomy tube (not shown) of a patient to suction mucus and other secretions or fluids from the patient's respiratory system. The closed suction catheter assembly 58 also includes, as shown in FIG. 11, a proximal end 66 and a proximal coupling 68 which retains the proximal end 70 of the protective sleeve 62 in position. The closed suction catheter assembly 58 also includes a valve mechanism 72 for selectively supplying suction through elongate aspirating catheter 60.

Referring now to FIG. 3, an annular projection 44 is disposed on the distal side 51 of base 50. The annular projection 44 is shown surrounding a channel 74 through which the aspirating catheter 60 may be advanced. As will be explained in more detail below, the annular projection 44 extends through the valve 40 (FIG. 2) of the HME 20 when the adaptor 42 is attached to the HME 20. Thus, the annular projection 44 is configured to hold open the projections 38 (FIG. 2). Such a configuration reduces the risk of mucus accumulating in HME 20, as the projections 38 are sufficiently distant from the catheter 60 so that mucus is not removed from the catheter 60 by the projections 38. If mucus accumulates in and is allowed to remain in the HME 20, it may interfere with the patient's breathing.

Figure 4:
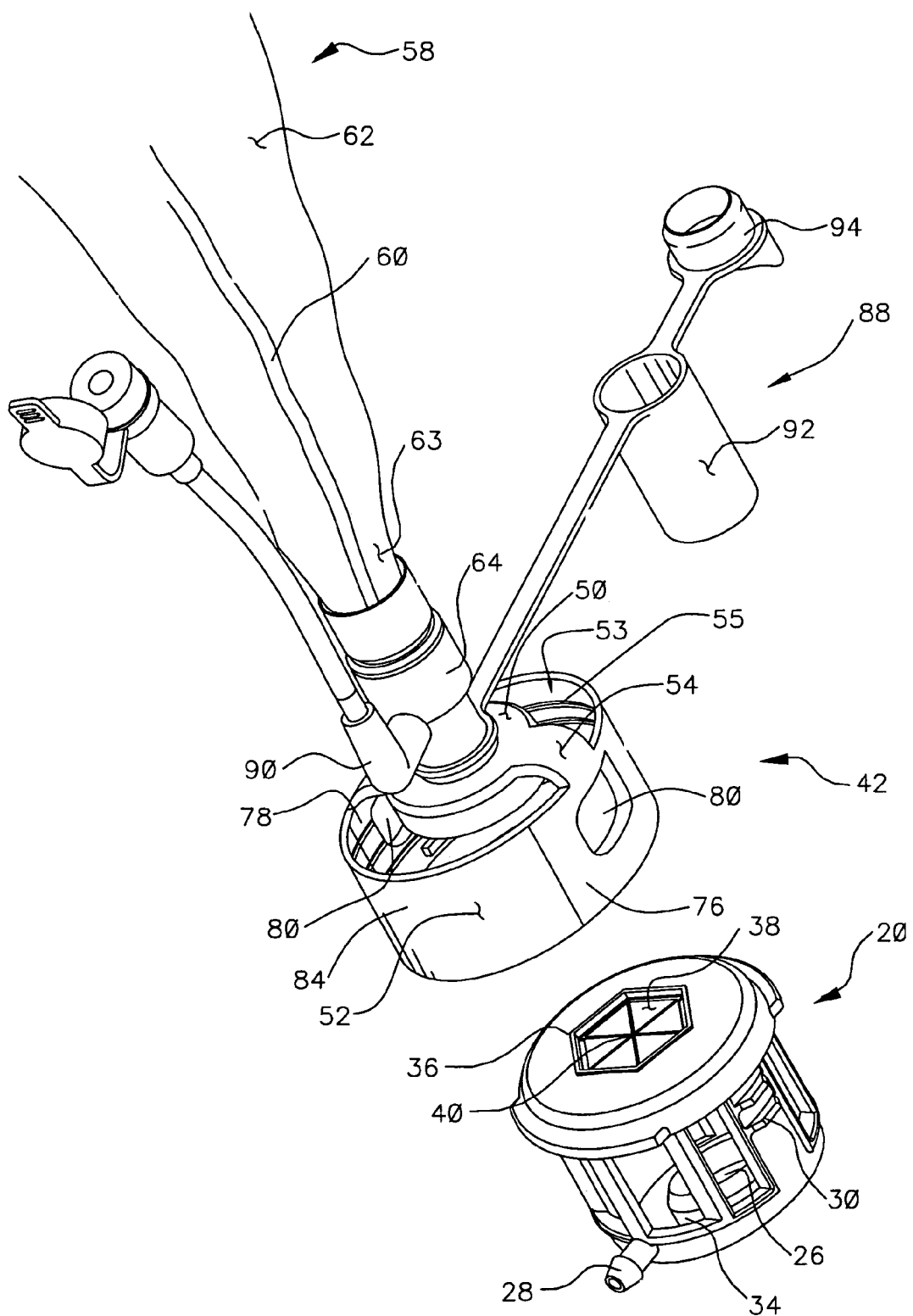
FIG. 4 is another perspective view of the adaptor shown in FIG. 3 in conjunction with an HME.
Figure 5:
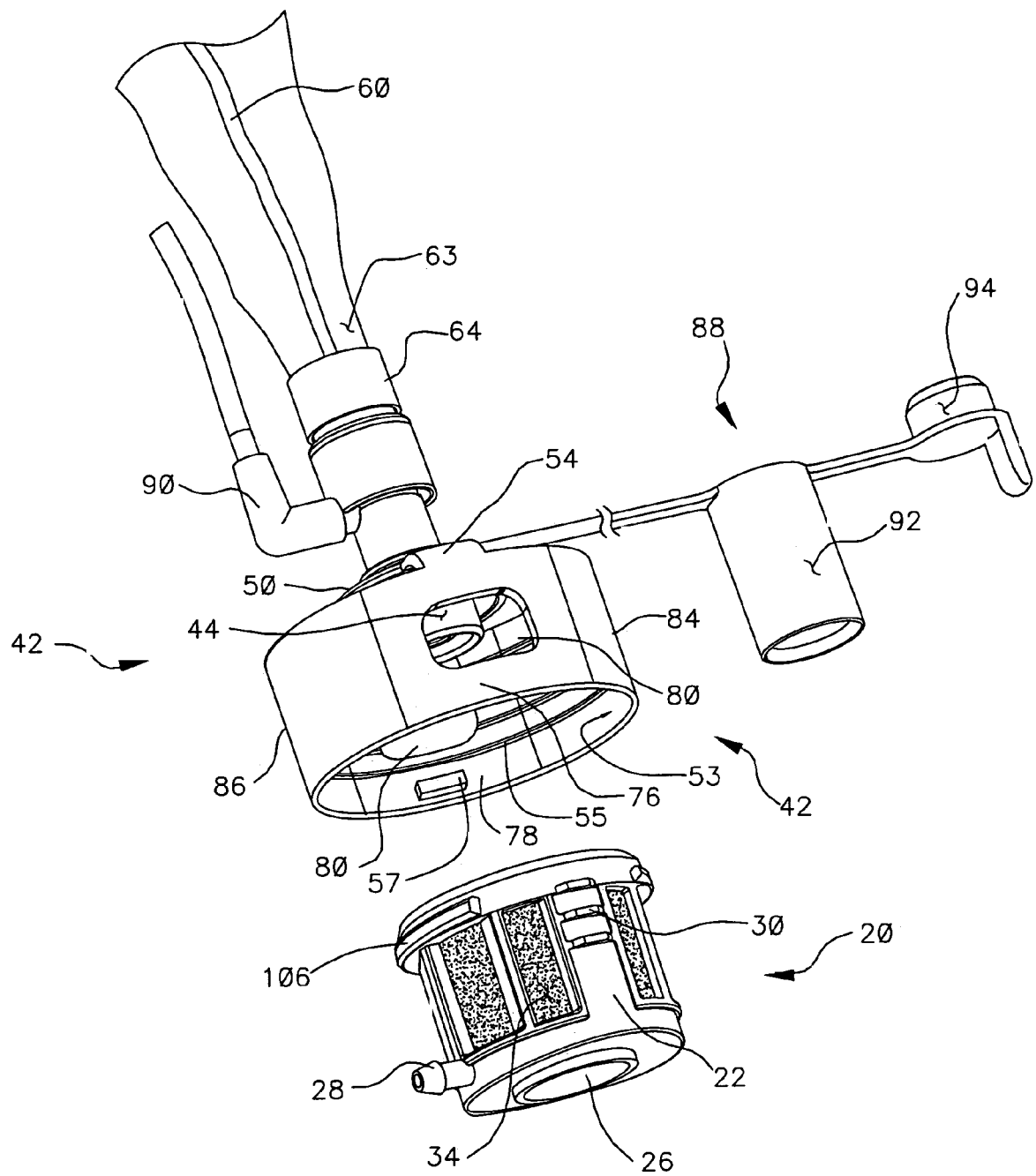
FIG. 5 is a perspective view of an HME and an adaptor positioned with respect to each other so that they may be easily connected to one another.
Figure 6:
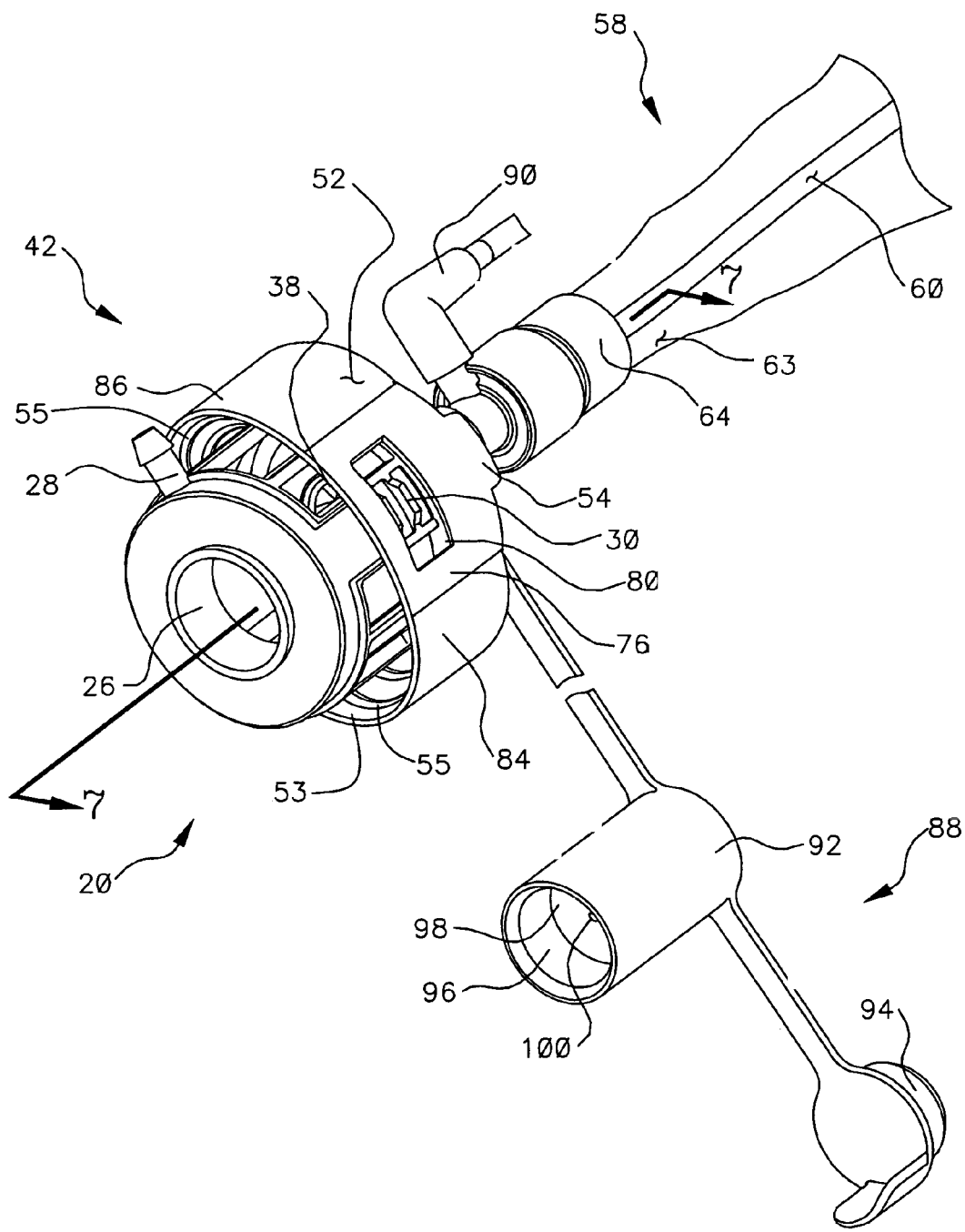
FIG. 6 is a perspective view of the adaptor shown in FIG. 5 with the HME nested within the adaptor.

In one aspect, the retainer 52 may be an annular wall and form four sections. As shown in FIG. 3, two of the four sections of the retainer 52, a first section 76 and a second section 78, are disposed on opposing sides of the retainer 52 and may be provided with an attachment mechanism 80 to attach the retainer 52 to the HME (not shown). In the aspect shown in FIG. 3, the retaining mechanism is an aperture 80 that is formed in the first and second sections 76 and 78, respectively, of the retainer 52. The apertures 80 are sized to engage the ridges 30 (FIGS. 4-6) of the HME 20 (FIGS. 4-6). Once the ridges 30 are engaged by the apertures 80, the adaptor 42 is securely attached to the HME 20. As discussed herein the attachment mechanism 80 in which apertures are present in the sides of the retainer 52 is optional.

As noted herein, the adaptor 42 is designed to be rotationally engaged with an HME 20. While there are a number of ways to rotationally interconnect the adaptor 42 and HME 20, all suitable ways are contemplated to be within the scope of the claims. Several of such ways are described herein, but the discussion is not intended to be all-inclusive or limiting with respect to any particular embodiment. For example, while a restrictive flange key 106 (FIGS. 5 and 8) as discussed below is one way, other suitable ways to promote rotational engagement are via elements such as threads (single or multiple lead), grooves, recesses, channels, troughs, and the like. Thus, while in the above described aspect of the present invention, the retainer has apertures 80 which may engage ridges 30 or other projections on the HME, it will be appreciated that the ridges 30 may take another form and/or may be designed to threadedly receive or engage leads 55 or the like located about all or a portion of the inner surface or wall 53 of the retainer 52 irrespective of whether they are to engage optional apertures 80.

The two remaining sections of the retainer 52 may include, in selected aspects, a third section 84 and a fourth section 86 which, as shown in FIGS. 3-6, may be deflectable or deformable or such that application of pressure thereto allows the first and second sections 76 and 78, respectively, to be able to outwardly bow from protrusions which may be present on the sides of the HME 20, thereby facilitating engagement and/or disengagement of apertures 80 or the like with those protrusions. The third section 84 and the fourth section 86 are situated between the first and second sections 76 and 78, respectively. In those embodiments having apertures 80 or the like, when the clinician desires to remove the adaptor 42 from the HME 20, he or she needs only to press the third and fourth sections 84 and 86, respectively, towards each other. This forces the retainer 52 to deform slightly and causes the first and second sections 76 and 78, respectively, to move outwardly and away from the HME 20. Movement of the sections 76 and 78 causes the apertures 80 to move a sufficient distance away from the ridges 30 so that the ridges 30 are no longer nested therein and engaged thereby. The retainer 52 may then be rotated to disengage the HME 20. Thus, the retainer 52 can be removed from the HME 20 without torque or force being applied to the HME or the artificial airway. The ability to remove the closed suction catheter assembly 58 while minimizing the application of any torque to the artificial airway is important, as a small amount of torque can cause irritation and discomfort to the patient. In some instances, the closed suction catheter assembly may be used numerous times a day. In these instances, a small amount of irritation can lead to increased patient discomfort.

It is also contemplated that some aspects of the present invention which do not include apertures 80 will include third and fourth sections 84, 86. As with the third and fourth sections described in the context of FIG. 3, they may be deflectable or deformable; however, in other aspects the third and fourth sections of the retainer 52 may be rigid or non-deformable. In all aspects of the present invention in which the third and fourth sections of the retainer 52 are present, each may also be threaded or the like as suggested by leads 55 in FIG. 5.

Because the closed suction catheter assembly 58 may often be removed from the artificial airway of the patient, an adaptor cover 88 may be provided. It is generally desirable for the catheter assembly 58 to be properly cleaned such that later use of the catheter may be performed without a decrease in efficiency. Normally, it will be desired for the aspirating catheter 60 to be positioned within the channel 74 when the catheter assembly 58 is removed from the patient. Even if the aspirating catheter 60 extends out of the channel 74 and has not been cleaned properly, the use of an adaptor cover 88 can help to prevent contamination of the aspirating catheter 60. The failure to properly clean the catheter assembly 58, and more specifically the distal end of the aspirating catheter 60 may result in mucus or other fluids drying thereon and preventing or restricting use thereof. As described in more detail herein, the introduction of saline or other suitable fluid through lavage port 90 facilitates cleaning of the catheter and catheter assembly, and reduces the chance of inoperability of the catheter or a decrease in performance.

As shown in FIG. 3, an exemplary adaptor cover 88 may be formed to include a first portion 92 and an end cap 94. The first portion 92 includes an elongated cylinder 96 with a wall 98 formed through the middle of the cylinder. A small opening 100 may be formed in the wall 98 to allow a very small amount of air into the first portion 92. Thus, the first portion 92 may be attached to the annular projection 44 after removal of the closed suction catheter assembly 58 after each suctioning procedure. If the adaptor 42 is fixed to the catheter assembly 58, then cover 88 must be configured so that first portion 92 has a sufficient length to extend into the adaptor 42. Once the aspirating catheter 60 has been cleaned, the end cap 94 may further be used to cover the opening 100 in the first portion 92. As is described in more detail herein, in the context of a flapper valve for extended use catheters (such as the 72-hour TRACH-CARE closed suction catheter available from Ballard Medical Products, a wholly owned subsidiary of the assignee of the present invention), the small opening 100 in wall 98 may provide or allow for turbulent cleaning of the catheter assembly or at least a portion thereof.

FIG. 4 shows a perspective view of the adaptor 42 and the HME 20 from the proximal or care-giver end of the closed-suction catheter assembly 58. FIG. 5 shows a close-up side view of the orientation of the adaptor 42 and the HME 20. FIG. 5 shows the alignment between the flange keys 106 of the HME 20 and an optional flange 57 of the retaining ring 52 of the adaptor 42. With the flange keys 106 and the retaining ring 52 in alignment with each other, the adaptor 42 need only be rotated until the retaining ring 52 engages the HME 20, and in this case the flange keys 106 of the HME 20. Alternately, if thread leads 55 or the like are present along the inner wall 53 of the retainer 52, the adaptor 42 may be rotated relative to the HME 20 until the thread leads 55 or the like engage the ridges 30 of the HME 20 or other suitable protrusion or recess thereon, in such a manner as to allow the HME 20 to be held securely to the adaptor 42. In those aspects of the present invention having apertures 80 the rotational movement and engagement of the adaptor 42 relative to the HME 20 may be continued until the ridges 30 or other suitable protrusion snap into the apertures 80 for the HME 20 to be held securely to the adaptor 42. As suggested above, a clinician may assist this process by pressing the third and fourth sections 84 and 86, respectively, toward each other to enable the ridges 30 to more easily engage the apertures 80. Alternatively, the housing 22 of the HME 20 may be flexed to slightly deform the housing 22 to enable the ridges 30 to more easily engage the apertures 80. Once the ridges 30 are positioned within the apertures 80, the housing may be allowed to return to its original position so as to retain or secure the HME 20 relative to the adaptor 42.

To release the adaptor 42 from the HME 20, the third and fourth sections 84 and 86, respectively, of the retaining ring 52 need only be squeezed momentarily to move the first and second sections 76 and 78, respectively, outwardly. This movement releases the ridges 30 from the apertures 80 and allows HME 20 to be disengaged from the adaptor 42. Those aspects not having apertures 80 may simply be rotated in the direction opposite that which was used to engage the adaptor 42 and the HME 20.

FIG. 6 is a close-up perspective view of the HME 20 seated within and engaged to the adaptor 42. As shown therein, the ridges 30 of the HME 20 are nested in the apertures 80 in the first and second sections 76 and 78, respectively, so that the retaining ring 52 is held securely to the HME 20. Because the apertures 80 in the retaining ring 52 are wider than the ridges 30, the adaptor 42 is able to rotate slightly in either direction. If desired, the apertures 80 could be made virtually the same size as the area covered by ridges 30 to reduce or prevent such rotation.

Figure 7:
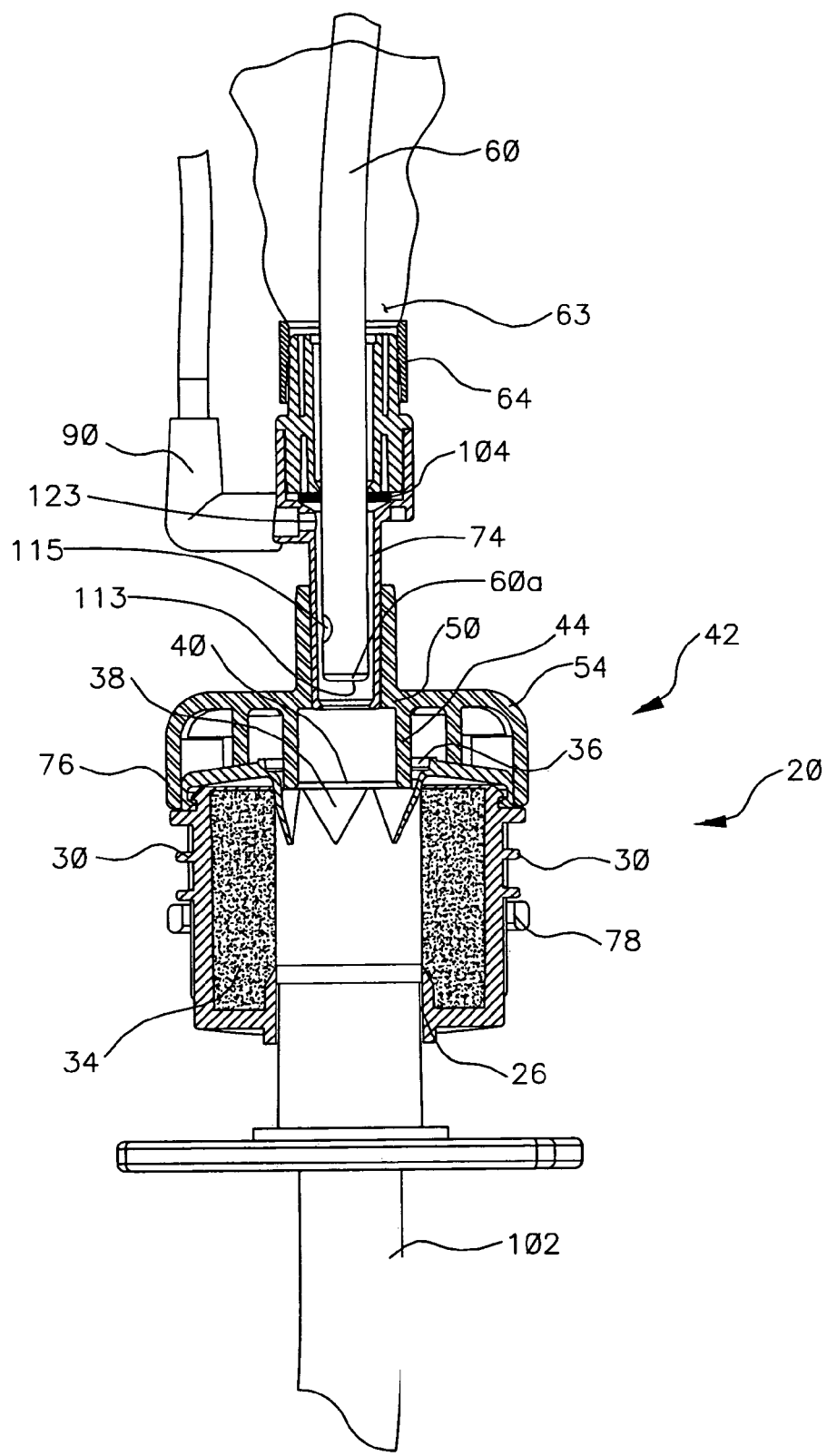
FIG. 7 is a partial cross-sectional view of the adaptor and HME shown in FIG. 6 taken along line 7-7 of FIG. 6, wherein the HME is mounted on an artificial airway, the artificial airway not being shown in FIG. 6.

FIG. 7 is a side partial cross-sectional view of the HME 20 and the adaptor 42 taken along line 7-7 in FIG. 6 through the ridges 30 and the apertures 80, as well as a fragmented view of the HME mounted on a tracheostomy tube 102. The adaptor cover 88 is not shown in this view. As shown in FIG. 3, the annular projection 44 is configured to engage the projections 38 of the valve 40 of the HME 20 so that the projections are moved to an "open" position, which is shown in FIG. 7, upon attachment of the adaptor 42 to the HME 20. If the projections 38 were to engage the aspirating catheter 60 as it is retracted from the tracheostomy tube 102, mucus and other secretions could be scraped from the aspirating catheter 60 by the projections 38. Such secretions would remain in the HME 20 and could drip back into the tracheostomy tube or coat the porous material 34 in the HME 20 and potentially interfere with the patient's breathing. By keeping the projections 38 in the "open" position, the annular projection 44 allows the mucus to remain on the aspirating catheter 60 until the aspirating catheter 60 engages a seal 104 of the closed suction catheter assembly 58. The seal 104, as shown in FIG. 7, is disposed within the closed suction catheter assembly 58 and engages the aspirating catheter 60 as the catheter is moved through the center of the annular seal 104. Mucus is stripped from the aspirating catheter 60 by the seal 104 as the aspirating catheter passes through the center of the annular seal 104. As discussed below multiple seals may be present.

Figure 7A:
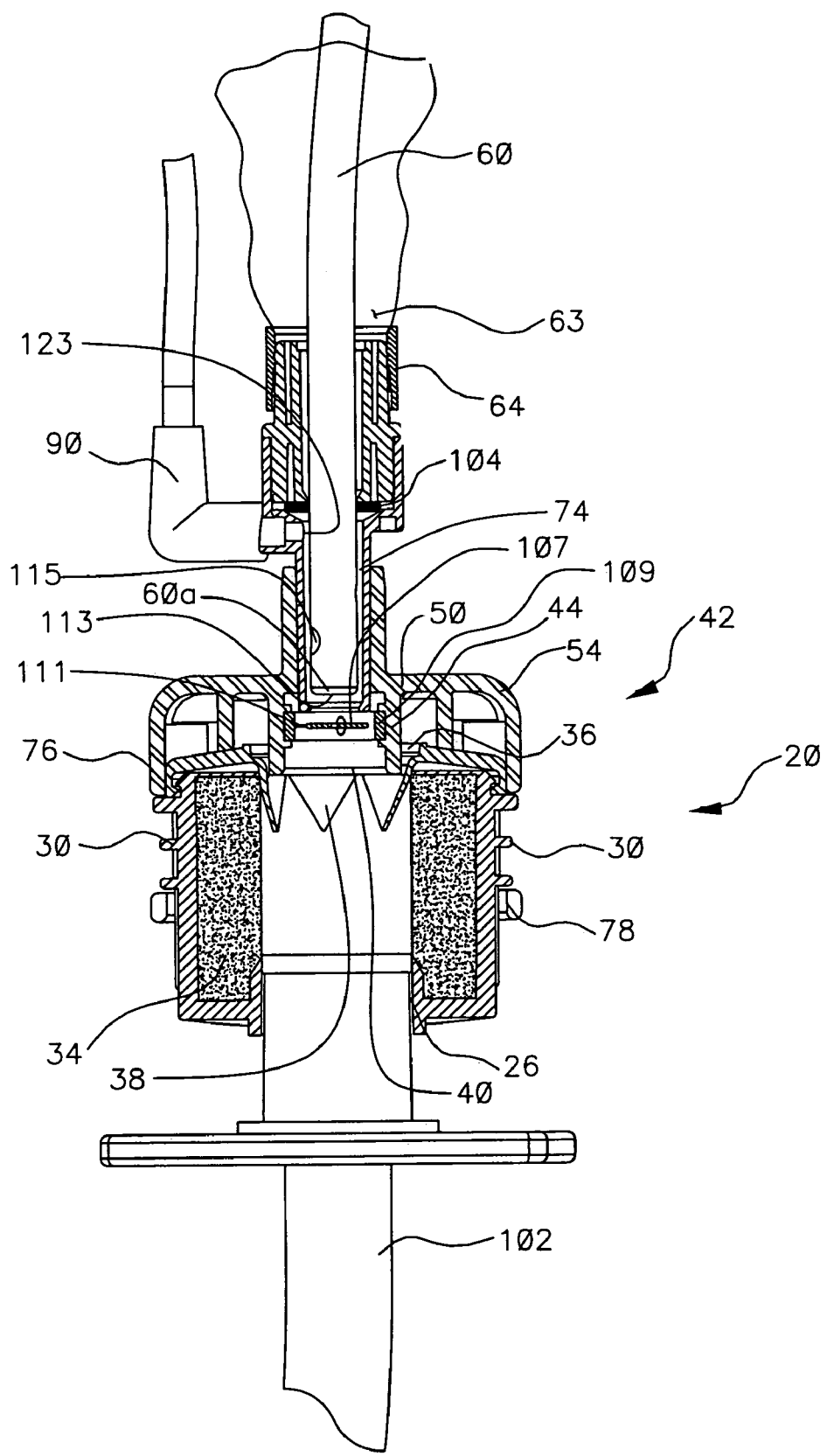
FIG. 7A shows a cross-sectional view of the adaptor and distal portion of a catheter of an improved respiratory suction catheter apparatus with a valve member in an open position in accordance with an aspect of the present invention.
Figure 7B:
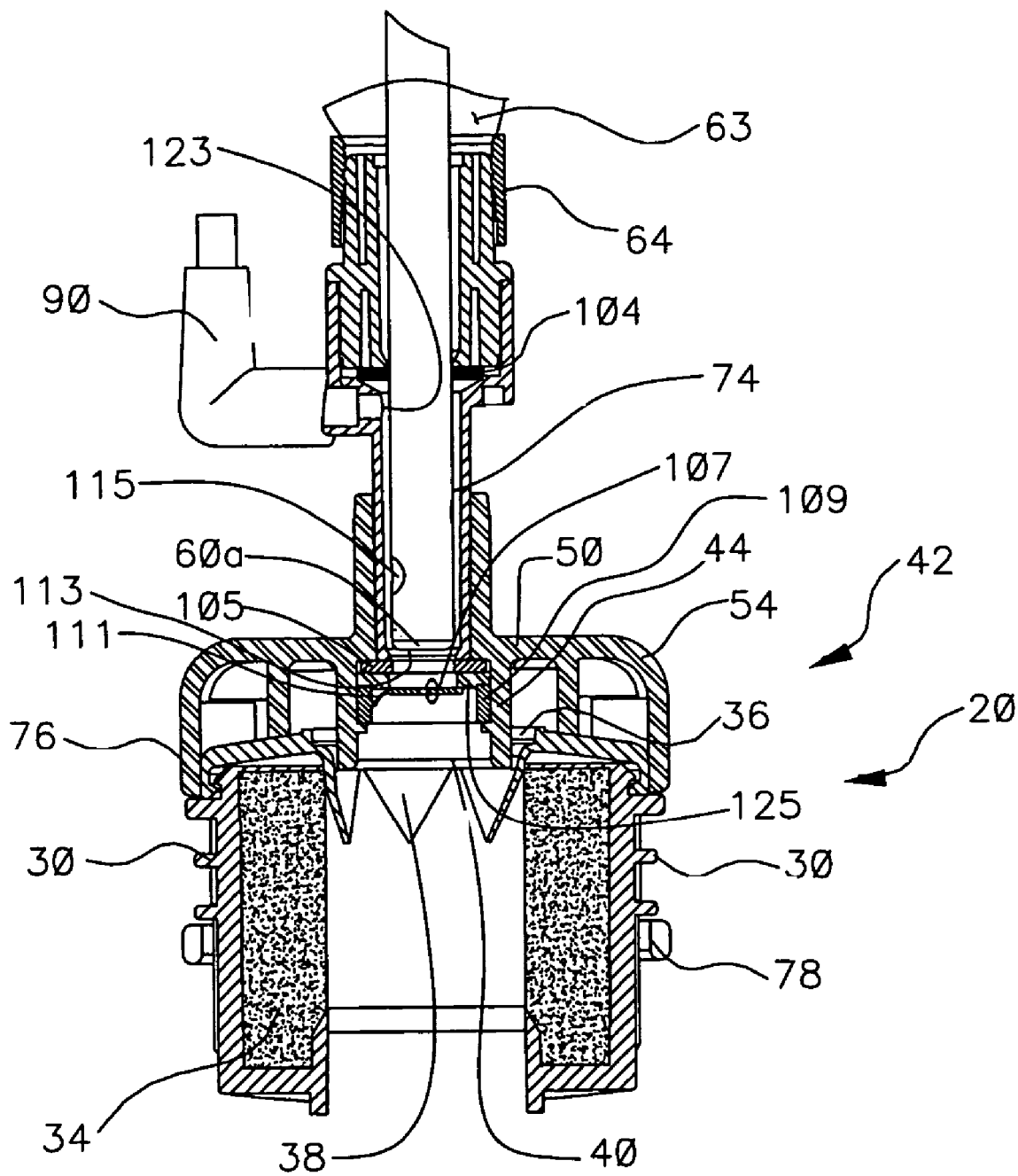
FIG. 7B shows a cross-sectional view of an adaptor and catheter portion similar to that shown in FIG. 7A, with the valve in a second, closed position.

FIGS. 7A and 7B are side partial cross-sectional views of an HME 20 and alternate adaptors 42 taken along lines similar to that of 7-7 in FIG. 6 through the ridges 30, as well as a fragmented view of the HME mounted on a tracheostomy tube 102. The adaptor cover 88 is not shown in either of these views. The aspects shown in FIGS. 7A and 7B are similar to that of FIG. 7 except that the catheter assemblies 58 are those of extended use closed suction catheters such as the TRACH-CARE 72* catheter. The aspect shown in FIG. 7B has a second PEEP seal 105 (similar to that of 104) and a cleaning chamber closing valve 107, whereas the aspect shown in 7A does not include the optional second PEEP or wiper seal 105. Although the description herein focuses on a flapper valve, the present invention contemplates that any number of suitable valve types and configurations may be included. The closed suction catheter assembly 58 of FIGS. 7A and 7B are configured similarly to those shown in FIGS. 5, 6, and 11 and are therefore numbered accordingly. The addition of the second PEEP seal 105 and/or valve 107 helps delineate a cleaning chamber which can enable turbulent cleaning of the aspirating catheter 60. The second seal 105 and valve 107 provide for such cleaning while the catheter assembly 58 is attached to the HME 20 without introducing lavage or cleaning fluids into the HME 20 and thereby prevents or reduces the prospects for contamination of the catheter 60 when not connected to an HME or other artificial airway device and where cover 88 is not present or in place. The use of an extended use catheter such as those described herein may provide certain benefits which in some instances may reduce or eliminate the need for the cover 88, while in other instances the cover may still be desirable.

It will be appreciated that the valve 107 should be positioned proximal to the distal end of the projection 44 of the adaptor such that the valve 107 may open and close without interfering with the valve 40 of the HME 20. Further discussion of an extended use catheter assembly which may be used in connection with one or more aspects of the present invention may be found at the end of the disclosure.

Figure 8:
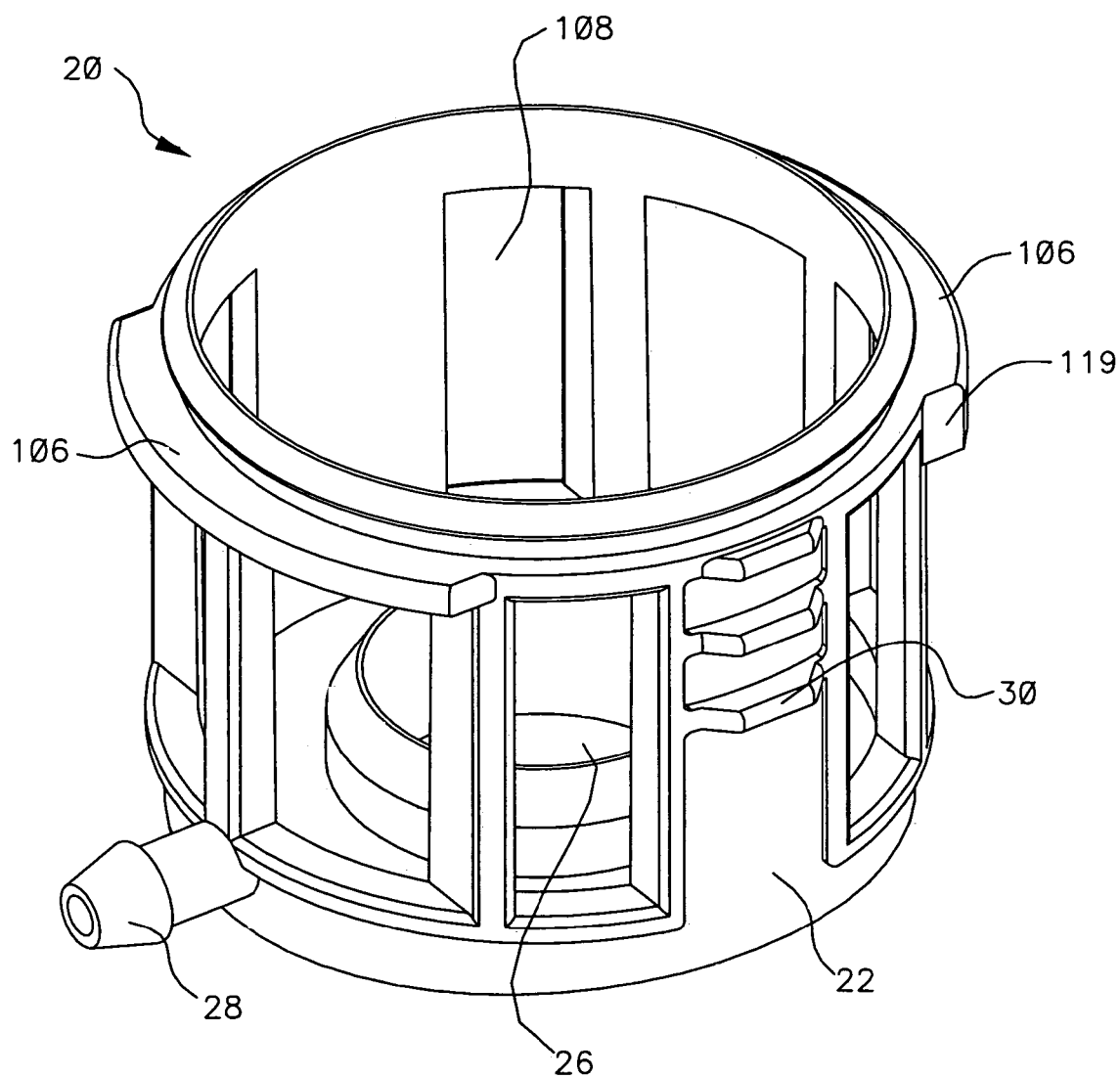
FIG. 8 is a perspective view of an HME with the cover of the housing removed.

FIG. 8 shows a perspective view of an HME 20 having a removable top surface or cover. The HME 20 shown in FIG. 8 includes a pair of flange keys 106 that are disposed near the top opening 108 of the HME 20, the flange keys 106 being disposed oppositely from each other along the exterior of the HME 20. The flange keys 106 may be in addition to or instead of the ridges or other protrusions. The flange keys 106 may be aligned with or offset from the ridges 30, if present. For example and as shown in FIG. 8, the flange keys 106 may be offset 90 degrees from the ridges 30. The flange keys 106 may be configured to fit between the HME housing 22 and the third and fourth sections 84 and 86, respectively, of a retaining ring 52 (FIGS. 3-6) when the adaptor 42 (FIGS. 3-6) is attached to the HME 20. When apertures 80 are present, the flange keys 106 may help to prevent the clinician or care giver from inadvertently orienting the adaptor 42 on the HME 20 so that the apertures 80 of the retaining ring 52 will not align with the ridges 30 when the two members are rotationally engaged. If the retaining ring 52 (FIGS. 3-6) is not in the proper orientation, the first and second sections 76 and 78, respectively, may contact the flange keys 106 or the top of the ridges 30 in such a manner as to prevent improper attachment of the HME 20 to the adaptor 42.

The flange keys 106 can also be used to assist with rotational engagement of the adaptor 52 and the HME 20, as discussed in more detail herein. Flange keys 106 may have a lip or stopper member 119, generally located at one end of the underside of the flange keys, which restricts further rotation of the retainer 52 relative to the HME 20. This is so even in those aspects of the HME 20 where ridges 30, threads, or projections other than the flange keys 106 are not present.

While ridges 30 are shown as being present on two portions of the housing 22 of the HME 20 opposite one another, the ridges may be continuous or spaced about the HME in any suitable orientation. As noted above, the ridges need not be such that they protrude through the retainer 52, but rather may retain a flange, thread leads or the like which may be provided on the inner surface 53 of the retainer 52. Further the ridges on the HME 20 may be of greater length or other design so as to facilitate rotational engagement of retainer 52 and the HME 20.

While discussed with respect to FIGS. 4 through 8 as being a retaining ring, those skilled in the art will appreciate that the retainer 52 need not be in the form of a ring. For example, the third and fourth sections 84 and 86, respectively, could be omitted from the retainer. In such an aspect, the first and second sections 76 and 78, respectively, will engage the HME 20. In such a configuration, a flange may be provided on each of the first and second sections 76 and 78, respectively, if necessary such as in those instances in which apertures 80 are designed to engage the ridges or projections on the HME 20. The flange would permit the first and second sections 76 and 78, respectively, to be pivoted or urged away from the HME 20 when the closed suction catheter assembly 58 is to be disengaged from the HME 20.

Figure 9:
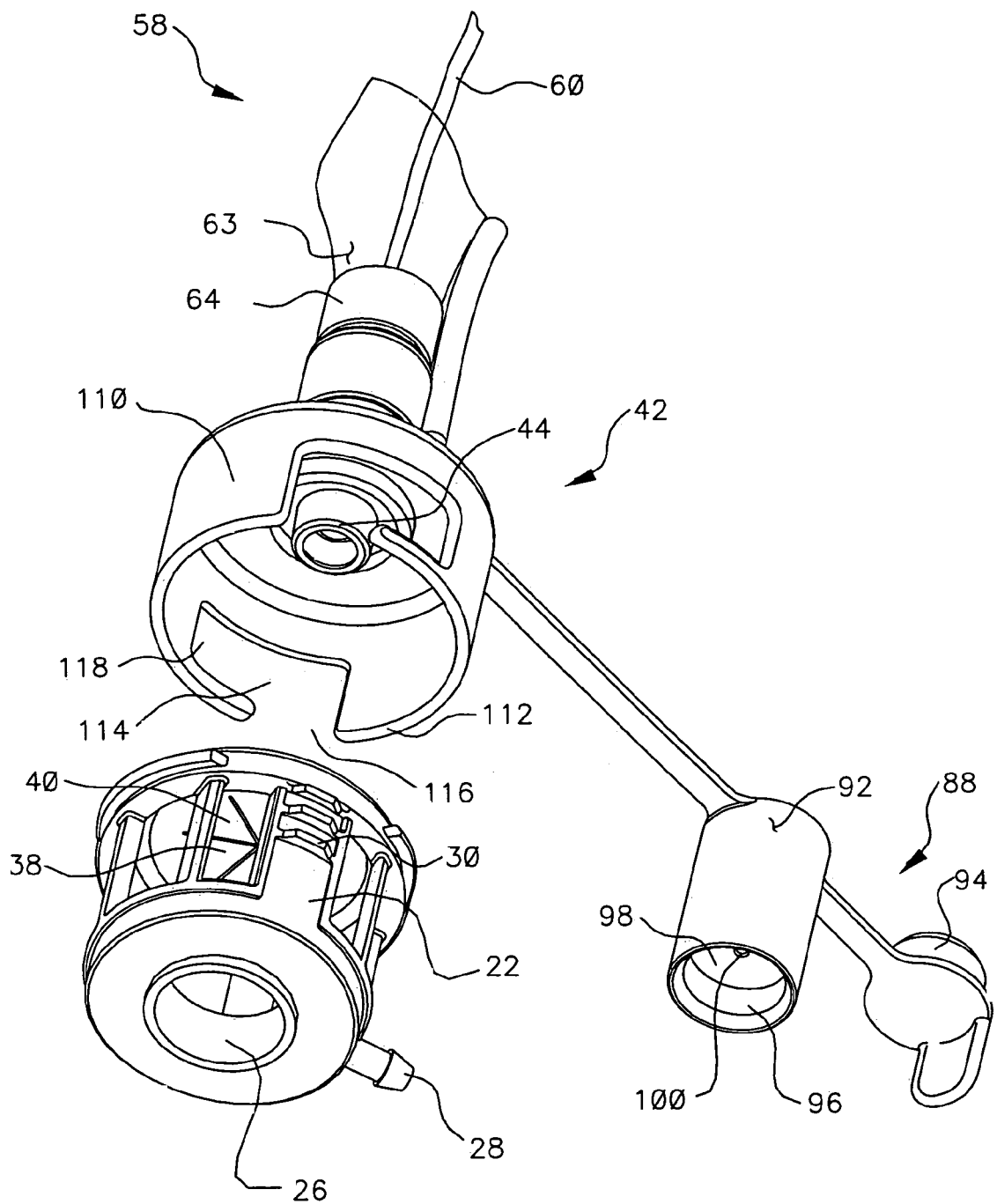
FIG. 9 is a perspective view of an alternate aspect of an adaptor made in accordance with the present invention.

Turning now to FIG. 9, there is shown therein a perspective view of an alternative aspect of an HME adaptor, generally indicated at 42, made in accordance with the principles of the present invention. As illustrated in FIG. 9, the retainer may be formed as a cup-shaped housing 110, the distal portion 112 of the housing 110 forming a retaining ring for encircling the HME 20. An L-shaped port or channel 114 extends into the housing 110 to receive a projection, in this case ridges 30.

Figure 10:
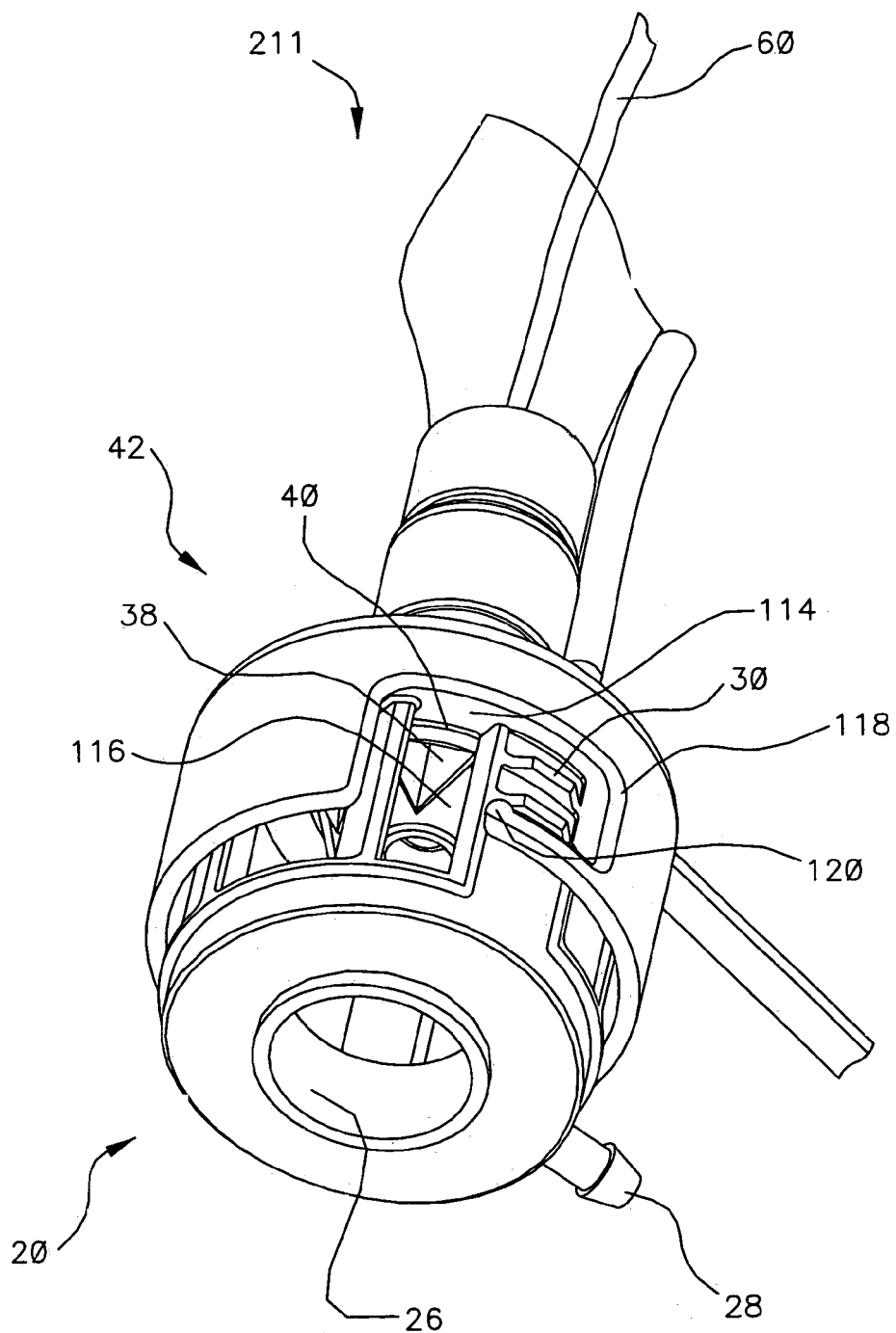
FIG. 10 is a perspective view of the invention shown in FIG. 9 with the adaptor mounted on the HME.

In the aspect depicted in FIG. 9, the ridges 30 are initially aligned with the first end 116 of the L-shaped channel 114. Once the ridges 30 have been sufficiently advanced into the L-shaped channel 114, the cup-shaped housing 110 can be rotated to place the ridges 30 at the second end 118 of the channel 114, as shown in FIG. 10. Once the ridges 30 are secured at the end 118 of L-shaped channel 114, the closed suction catheter assembly 58 can be used in the conventional manner. As above, alternate aspects of the HME 20 may contain projections other than ridges 30.

The ridges 30 at the end 118 of the channel 114 may be maintained in place in a variety of ways, including friction, or a lip 120 (FIG. 10) or another mechanism which inhibits inadvertent counter-rotation and thus removal of the ridges 30 from the channel 114. FIG. 10 illustrates an interlocking arrangement of the HME 20 and the adaptor 42. Those skilled in the art will appreciate that there are numerous holding mechanisms that can be used in such a channel. These include, but are not limited to, a nonlinear path within the channel, a skid resistant surface along some portion of the channel, as well as a snap-fit or press-fit engagement between the channel and the ridges 30. It will be appreciated that the ridges 30 illustrated in FIGS. 9 and 10 may be replaced by any other suitable member or protrusion that provides for the bayonet lock style retention suggested by the ridges 30 and the L-shaped channel 114.

As with the aspects shown in FIGS. 3 and 9, adaptor 42 includes an annular projection 44 through which the aspirating catheter 60 may be advanced. The annular projection 44 holds open the projections 38 that form the valve 40 in the HME 20, thus preventing mucus from being deposited in the HME 20.

FIG. 11 shows a side view of a closed suction catheter system containing a closed suction catheter assembly 58 with an HME adaptor 42 and an alternate embodiment of the adaptor cover 88. The cover 88 may be attached to the valve 72 of the closed suction catheter assembly 58, but may be otherwise attached to the closed suction catheter assembly 58. The cover 88 has a first portion (not shown) which is substantially the same as the first portion 92 that is shown in FIGS. 3-9. The cover 88 as shown in FIG. 11 allows the closed suction catheter assembly 58 to form a loop with the adaptor 42. When the catheter assembly 58 is not being used, the ability to form the catheter assembly 58 and the adaptor 42 into a loop allows the catheter assembly 58 to be conveniently hung somewhere out of the way of the care-giver and the patient, but available for immediate use. FIG. 11 does not show such a loop, but instead shows cover 88 being unattached to adaptor 42.

Referring again to FIG. 7A and one exemplary aspect of a suitable extended use catheter. As noted above, the channel 74 is configured to allow the catheter 60 to slide therethrough and into and through the HME 20 to enable suctioning of the patient. At the completion of suctioning, the catheter 60 is desirably pulled back into the channel 74 to prevent interference with the respiratory circuit. While previous catheters have included a seal or collar to help wipe heavy layers of mucus or other secretion from the outside of the catheter and/or lavage ports for injecting lavage/cleaning solution through the lavage port 90 to further remove the secretions from the exterior of the catheter 60, it is still common to have secretions build up on the distal end 60a of the catheter 60. If such build up is not promptly removed, it can interfere with the ability of the catheter to properly suction the patient. It can also serve as a culture medium for pathogens within the closed suction catheter system. Such buildup limits the duration of use of such a catheter.

In accordance with one of the aspects of the present invention, it has been found that selective obstruction of the airflow into the distal end 60a of the catheter 60 significantly improves catheter cleaning. Additionally, it has been found that such a mechanism for improved cleaning also minimizes the withdrawal or air from the respiratory circuit.

One exemplary manner to achieve the improved cleaning discussed herein, is that which is shown in FIG. 7A, wherein a flap 107 is hingedly attached to a collar or annular ring 109 disposed inside the annular protrusion 44 so as to enable the flap 107 to pivot with respect to the ring to form a self-closing valve member. Of course, the flap 107 could be attached directly to the wall defining the annular protrusion 44. The hinged attachment 111 allows the flap 107 to selectively move while maintaining alignment with the catheter tip, thereby creating a self-closing flap valve. It should be recognized that while the valve or in this case the flap 107 is inside the annular protrusion 44, it should be positioned such that the valve or flap 107 does not interfere with the ability of the valve 40 of the HME to function.

Alternately, the valve or in this case the flap 107 could be positioned inside or at the distal end of the channel 74. As with a valve or flap positioned in the annular protrusion 44 the valve or flap 107 should be sized and positioned such that it does not interfere with the ability of the valve 40 of the HME to function.

As shown in FIG. 7B, the flap 107 is positioned to align with the distal end of the channel 74 when the catheter is withdrawn into the channel 74. The hinged attachment 111 may be sufficiently flexible that suction through the distal end 60a of the catheter 60 will draw the flap 107 proximally from a first, distal position into a second, proximal position, wherein the flap may come in contact with the distal end of the channel. Thus, with the flap 107 and related structures form a self-closing valve wherein no additional external manipulation of the catheter system is needed to close the valve.

As with many closed suction catheters, the catheter 60 includes a primary aperture 113 in the distal end 60a and one or more lateral apertures 115 positioned slightly proximal from the distal end.

When the flap 107 moves proximally and contacts the distal end of the channel 74, the flow of air entering the channel 74 is dramatically reduced or eliminated. When suction is applied to the catheter 60 while the air flow into channel 74 is reduced, the suction force serves to draw the available fluids-air mixture (e.g., air, secretions, lavage/cleaning solution, etc.) about the catheter 60 into aperture 113 while creating a negative pressure about the outside of the catheter. The negative pressure is believed to draw some of the fluid-air mix out of lateral apertures 115. The air that is suctioned or pulled out of lateral apertures 115 is then pulled towards distal catheter aperture 113. Thus, a continuous or circular flow path or pattern is established. It has been found that this pattern causes a significant turbulence in the fluid-air mixture around the outer circumference of the catheter tube 60. This turbulence greatly enhances the cleaning effect of the lavage/cleaning solution as secretions contained between the outside of the catheter 60 and the interior of the channel 74 are generally dislodged and pulled into aperture 113 and eventually down catheter 60.

While the flap may be substantially planar, the flap, for example, may also have a channel 117 (FIG. 7C) thereon which prevents the flap 107 from forming an airtight engagement with the distal end of the channel 74 or an aperture 121 (FIG. 7D) formed therein so as to allow a relatively small amount of air to pass through the flap. In other words, the channel 117 or an aperture 121 in the flap ensures that a measured volume of air will be drawn into the aperture 113 at the distal most end 60a of the catheter 60. The measured volume of air allowed to pass through channel 117 or aperture 121 in the flap is frequently called make-up air and is intended to avoid the situation where there is an absence of air or fluid in the channel 74 which would inhibit the ability to create turbulent air flow so as to provide the desired turbulent cleaning effect. Other ways of introducing make-up air or fluids are also contemplated.

As noted above, the measured volume of air which is drawn in through the channel 117 or aperture 121 in the flap can have an important effect. Specifically, the air allows for the creation of turbulent airflow both within the catheter 60 and immediately around its exterior. The turbulent airflow in turn, assists in breaking up agglomerations of mucus and secretions which lavage/cleaning solution alone may not. Thus, the turbulent airflow helps to provide improved cleaning of the distal end 60a of the catheter 60. This is in sharp contrast to many of the prior art devices which have advocated the use of a lavage/cleaning chamber to clean the exterior of the catheter. Because the lavage/cleaning chamber is usually substantially larger than the catheter or because makeup air is not specifically provided, it is difficult to create turbulent airflow within the chambers of previous devices. Without turbulent airflow, the mucus and other secretions are often not removed from the exterior of the catheter.

Figure 7C:
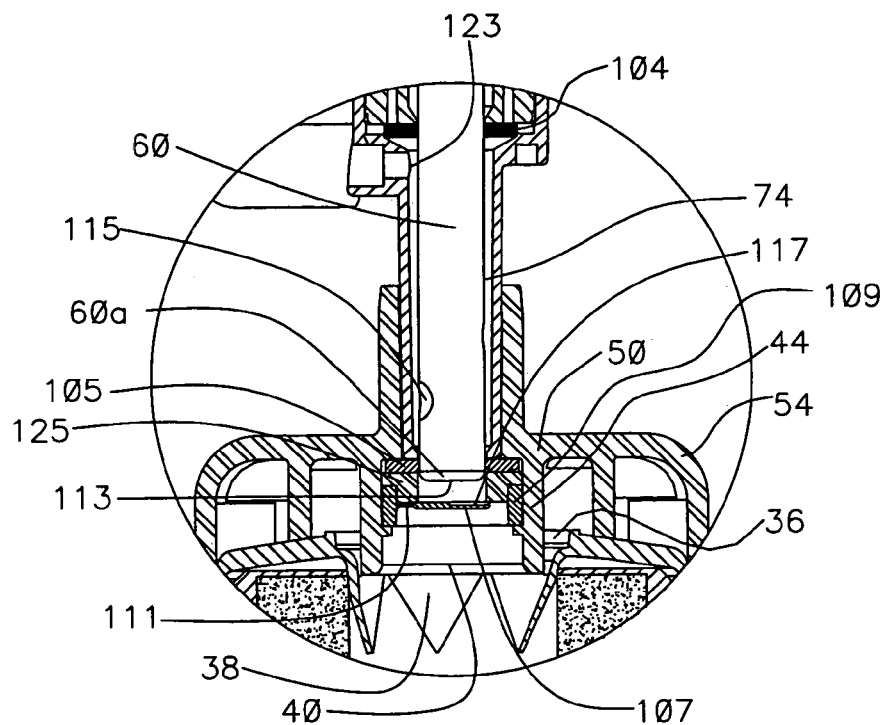
FIG. 7C shows a fragmented, close-up cross-sectional view of one aspect of the improved respiratory suction catheter apparatus similar to that shown in FIG. 7A.
Figure 7D:
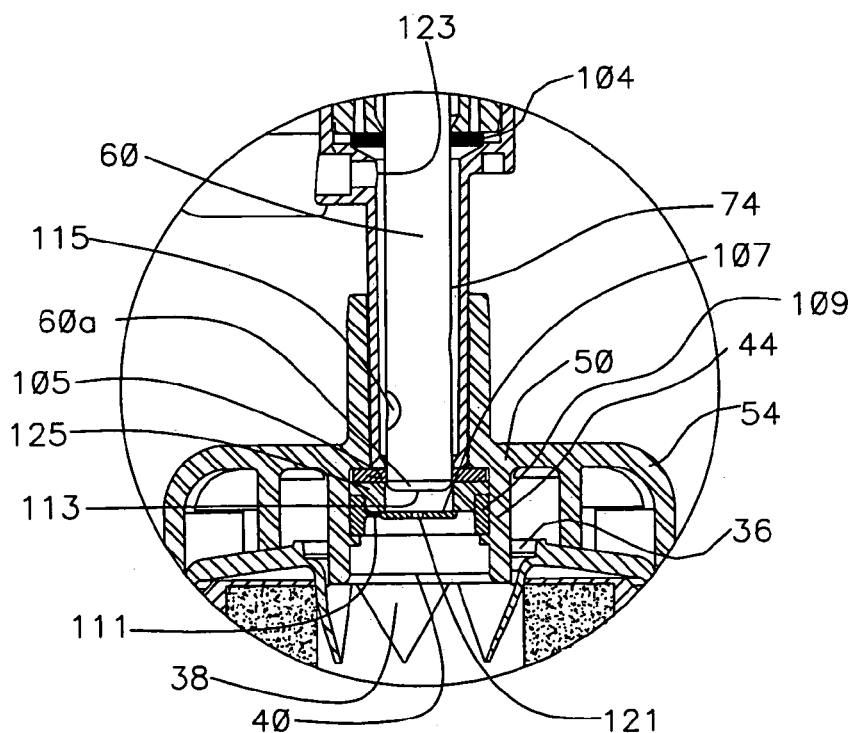
FIG. 7D shows a fragmented, close-up cross-sectional view of another aspect of the improved respiratory suction catheter apparatus similar to that shown in FIG. 7A.

While shown in FIG. 7A as being capable of engaging the distal end of the channel 74, the flap 107 forming a valve need not engage the channel itself. Thus, for example, FIGS. 7B-7D show aspects similar to those shown in FIG. 7A, except that the flap 107 is disposed to engage the distal end of a spacer 125 between a second wiper seal 105 and an annular ring 109 rather than the distal end of the channel 74. It will be appreciated that numerous other configurations are also possible. Other exemplary configurations will have the flap close on to the distal end of a second wiper seal, onto the distal end of the annular ring 109, or onto a latch or catch which may extend inwardly from the annular ring 109.

Desirably, a source of makeup air will be provided. This can be accomplished by using either of the flap configurations shown in FIGS. 7C and 7D. In the alternative, a small hole can be formed in the annular ring 109 to facilitate a small amount of makeup air being present to enhance suction flow and to increase turbulence.

Regardless of which configuration of those shown in FIGS. 7A through 7D is used, the result is an improved ability to clean the distal end 60a of the catheter 60, while at the same time significantly reducing the amount of air which is withdrawn from the ventilation circuit. Thus, consistent ventilation may be provided to the patient, and the clinician is able to more easily clean the catheter 60 without concern of the lavage or cleaning solution from entering the patient, the artificial airway, and more specifically the HME.

Having described several aspects of an extended use closed suction catheter assembly, the disclosure turns to a description of the use and functioning of one aspect thereof. In use the flap will extend inwardly from an annular ring 109, the wall of the channel 74, or the wall of the annular protrusion 44. The flap 107 is desirably hingedly attached to either the wall directly or to the annular ring 109. When no suction is applied to the catheter 60, or when the distal end 60a of the catheter is disposed distally from the flap 107, the flap will generally extend distally from the annular ring 109 and provide virtually no resistance to advancement of the catheter 60.

While discussed above as requiring suction, those skilled in the art will appreciate that the flap 107 could be configured to bias the flap into the proximal or closed position. In any instance, to open or release the flap 107, the catheter 60 may be advanced with sufficient force to cause flap 107 to pivot distally thereby allowing the catheter 60 to advance further into the artificial airway of the patient. In some aspects, where a catch or the like (not shown) is in communication with the flap 107, it may be necessary for the catheter to be advanced with additional pressure so as to deflect the catch or lock out of the way.

Those skilled in the art will appreciate that numerous modifications could be used to accomplish the principles of the present invention. As an example, a single arm and multiple catches could be used with the flap 107. Likewise, the flap could be attached to a ring or wall by a pair of arms. Furthermore, whether one or more arms were present the arms could be configured to bias the flap into a closed or occluding position.

As mentioned above, a catheter assembly 58 may have a first wiper seal 104 and an optional second wiper seal 105. As the catheter 60 is withdrawn past the distal most wiper seal 105, the wiper seal removes major secretions. While discussed herein as a wiper seal, some other structure having close tolerances (i.e. one which would remove most secretions) could also be used.

From the wiper seal 105, the channel 74 extends proximally and forms a cleaning chamber. It will be appreciated from the discussion herein that flap 107 may form the distal end of the cleaning chamber and thus distal wiper seal 105 while desired, is optional. In the aspects shown in FIGS. 7B-7D, disposed a short distance proximal from wiper seal 105 and forming the other end of the cleaning chamber is the other wiper seal 104. As with the distal most wiper seal 105, the object of the proximal wiper seal 104 is to remove secretions from the exterior of the catheter 60 as it is withdrawn from the artificial airway of the patient. However, the proximal wiper seal 104 will typically have a smaller diameter opening so that it more closely engages the exterior of the catheter 60 than the distal wiper seal.

In practice, as the catheter 60 is withdrawn into the channel 74 into a cleaning position, the flap 107 closes (either due to a bias or the suction through the catheter) to occlude or selectively isolate the opening in the annular protrusion 44 or channel 74. As the catheter 60 is withdrawn proximally out of the artificial airway and past the wiper seal 105, the distal end 60a of the catheter is wiped by the wiper seal 105 and/or the flap valve 107 or an optional protrusion (not shown) on the flap, so that most secretions on the catheter are removed. The secretions which are removed by the wiper seal 105 and other components may then be removed through the catheter 60.

Once the distal end 60a of the catheter 60 has advanced beyond the distal wiper seal 105, a bottle (not shown) may be attached to the lavage port 90 and a cleaning liquid (typically water) can be supplied through the side opening 123 in the channel 74. The cleaning liquid flows around the distal end 60a of the catheter 60 and cleans those secretions which were not removed by the distal wiper seal 105 from the distal end of the catheter. At the same time, the channel(s) 117 or aperture(s) 121 in the flap 107 allow a small amount of air into the catheter, thereby facilitating removal of the secretions.

By use of these various configurations, the cleaning of the distal end of a catheter can be enhanced while minimizing or eliminating the air drawn from the ventilation circuit of the patient. Additional information and embodiments with respect to extended use closed suction catheters of the type described herein may be found in U.S. Pat. No. 6,227,200 to Crump et al. and assigned to Ballard Medical Products, a whole owned subsidiary of the assignee of the present invention, and U.S. Pat. No. 6,602,219 to Madsen et al. and assigned to Kimberly-Clark Worldwide, the assignee of the present invention.

Each of the patents, applications, and/or references mentioned, referred to, or discussed herein is herein incorporated by reference in its entirety.

While various patents and other reference materials have been incorporated herein by reference, to the extent there is any inconsistency between incorporated material and that of the written specification, the written specification shall control. In addition, while the invention has been described in detail with respect to specific aspects thereof, those skilled in the art, upon obtaining an understanding of the invention, may readily conceive of alterations to, variations of, and equivalents to the described aspects and the processes for making them. It is intended that the present invention include such modifications and variations as come within the scope of the appended claims and their equivalents.

We claim:

1. An adaptor for connecting a closed suction catheter assembly having an aspirating catheter to a heat and moisture exchanger having an aperture formed therethrough, the adaptor comprising: a first end in communication with a distal end of the closed suction catheter assembly having an aspirating catheter; a second end adapted to rotationally engage the heat and moisture exchanger having an aperture formed therethrough; and the adaptor defining a channel formed through the adaptor so that the aspirating catheter of the closed suction catheter assembly is movable through the adaptor and through the aperture of the heat and moisture exchanger.

2. The adaptor according to claim 1, wherein the second end includes an inner wall.

3. The adaptor according to claim 2, wherein the wall is configured to encircle and receive the heat and moisture exchanger.

4. The adaptor according to claim 2, wherein the wall has at least one element adapted to engage at least a portion of an exterior surface of the heat and moisture exchanger, so as to enable retention of the adaptor relative to the heat and moisture exchanger.

5. The adaptor according to claim 2, wherein the second end is adapted to threadedly engage the heat and moisture exchanger.

6. The adaptor according to claim 1, wherein the second end is a retaining ring having: a first portion and a second portion, the first and second portions oppositely disposed from each other and configured to engage the heat and moisture exchanger; and third and fourth portions being oppositely disposed from each other on the ring between the first and second portions of the ring and being responsive to inwardly applied pressure so as to cause the first and second portions to bow outwardly, thereby providing for facilitation of engagement or disengagement of the first and second portions from the heat and moisture exchanger.

7. The adaptor according to claim 6, wherein the first and second portions define apertures for receiving external projections of the heat and moisture exchanger.

8. The adaptor according to claim 1, wherein the second end comprises at least one L-shaped channel configured for receiving external projections of the heat and moisture exchanger.

9. The adaptor according to claim 1, wherein the adaptor further comprises an annular projection configured for engaging a valve in a top of the heat and moisture exchanger.

10. An adaptor assembly for connecting a closed suction catheter assembly to a heat and moisture exchanger, the adaptor assembly comprising: an adaptor comprising a first end configured for communication with a closed suction catheter assembly, and a second end configured for engaging the heat and moisture exchanger, the adaptor further comprising a retainer configured to rotationally engage the heat and moisture exchanger; an annular projection defining a channel through the adaptor through which a catheter of the closed suction catheter assembly may be advanced; and a cover removably attachable to the annular projection.

11. The adaptor assembly according to claim 10, wherein the cover has a cylindrical wall formed therein and wherein the cover further contains at least one opening formed in the cylindrical wall.

12. The adaptor of claim 10 wherein the closed suction catheter assembly comprises: an elongated catheter having a proximal and distal end; the catheter system being adapted for communication with a patient's artificial airway so as to allow the catheter to be advanced through the artificial and into the respiratory tract of the patient; a valve member comprising a flap which is pivotable between open and closed positions and which is disposed adjacent the catheter to selectively isolate the catheter from the artificial airway; and first and second wiper seals disposed for engaging the catheter as it Is retracted through the artificial airway, the first seal wiper seat being disposed distally from the second wiper seal.

13. The adaptor of claim 12, wherein the catheter is retractable so that the distal end of the catheter is disposed between the first and second wiper seals.

14. The adaptor of claim 13, further comprising a lavage port disposed for releasing cleaning fluid onto the catheter, the lavage port being disposed distally from the first wiper seal.

15. A closed suction catheter system comprising: a closed suction catheter assembly having a catheter and a protective sleeve enveloping the catheter, the closed suction catheter assembly including a distal end; and a heat and moisture exchanger adaptor disposed at the distal end of the closed suction catheter assembly, wherein the adaptor is rotationally engageable with a heat and moisture exchanger.

16. The closed suction catheter system of claim 15, wherein the adaptor comprises: a base having a first end in communication with the closed suction catheter assembly, and a second end configured for engaging the heat and moisture exchanger and positioning the closed suction catheter assembly with respect to the heat and moisture exchanger; a retaining structure configured with the base to rotationally engage the base with the heat and moisture exchanger; and a channel defined through the base so that a catheter of the closed suction catheter assembly is movable through the base and the heat and moisture exchanger and into an artificial airway connected to the heat and moisture exchanger.

17. The closed suction catheter system according to claim 16, wherein the adaptor contains an annular projection configured for engaging a valve in the proximal end of the heat and moisture exchanger.

18. The closed suction catheter system according to claim 16, wherein the retaining structure comprises a first wall and a second wall, each of the walls having an aperture capable of selectively engaging projections extending outwardly from the heat and moisture exchanger.

19. The closed suction catheter system according to claim 16, wherein the retaining structure comprises a retaining ring having at least one element adapted to engage at least a portion of the heat and moisture exchanger, so as to enable retention of the retaining structure relative to the heat and moisture exchanger.

20. The closed suction catheter system according to claim 18, wherein the heat and moisture exchanger adaptor further comprises a cover.

21. The closed suction catheter system according to claim 18, wherein the heat and moisture exchanger adaptor is releasably engaged with the distal end of the closed suction catheter assembly.

22. The closed suction catheter system according to claim 15, wherein the closed suction catheter assembly comprises: an elongate catheter having a proximal end and a distal end, the catheter being advanceable through the adaptor and an artificial airway; and a cleaning chamber disposed adjacent to the adaptor, the cleaning chamber having a first wiper seal and a valve having an open position and a closed position, the first wiper seal being disposed at the proximal end of the cleaning chamber and the valve being disposed to substantially isolate the distal end of the catheter from the artificial airway when the distal end of the catheter is disposed in the cleaning chamber and the valve is in the closed position.

23. The closed suction catheter system according to claim 22, wherein the cleaning chamber further comprises a second wiper seal, the second wiper seal being disposed distally from the first wiper seal.

24. The closed suction catheter system according to claim 23, wherein the valve defines a distal end of the cleaning chamber.

25. The closed suction catheter system according to claim 22, further. comprising a lavage port having an opening disposed in fluid communication with the cleaning chamber, the opening being disposed distally of the first wiper seal.

26. The closed suction catheter system according to claim 22, where in the cleaning chamber includes a collar disposed proximal the distal end of the catheter assembly and distal the first wiper seal.

27. The closed suction catheter system according to claim 26, wherein the collar has a bore extending therethrough and through which the catheter may be advanced, and a pivotable flap for selectively covering the bore.

* * * * *